(12) United States Patent
Sailor et al.

(10) Patent No.: US 7,903,239 B2
(45) Date of Patent: Mar. 8, 2011

(54) POROUS PHOTONIC CRYSTAL WITH LIGHT SCATTERING DOMAINS AND METHODS OF SYNTHESIS AND USE THEREOF

(75) Inventors: Michael J. Sailor, La Jolla, CA (US); Michael P. Schwartz, Boulder, CO (US); Sara Alvarez, Oceanside, CA (US); Sangeeta Bhatia, Lexington, MA (US); Austin Derfus, San Diego, CA (US); Benjamin Migliori, La Jolla, CA (US); Lin Chao, Del Mar, CA (US); Yang Yang Li, Irvine, CA (US); Rebecca Campbell, La Jolla, CA (US); Jason Dorvee, Ithaca, NY (US); Ulla Camilla Rang, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 682 days.

(21) Appl. No.: 11/665,613

(22) PCT Filed: Oct. 19, 2005

(86) PCT No.: PCT/US2005/037572
§ 371 (c)(1),
(2), (4) Date: Feb. 25, 2008

(87) PCT Pub. No.: WO2006/044957
PCT Pub. Date: Apr. 27, 2006

(65) Prior Publication Data
US 2008/0212068 A1    Sep. 4, 2008

Related U.S. Application Data

(60) Provisional application No. 60/620,121, filed on Oct. 19, 2004.

(51) Int. Cl.
*G01N 1/00* (2006.01)
(52) U.S. Cl. .......................................................... 356/38
(58) Field of Classification Search ..................... 356/38
See application file for complete search history.

(56) References Cited

U.S. PATENT DOCUMENTS
5,318,676 A    6/1994   Sailor et al.
(Continued)

FOREIGN PATENT DOCUMENTS
WO    WO 00/03230    1/2000

OTHER PUBLICATIONS

S. Chan et al., "Porous Silicon Microcavities for Biosensing Applications", *Physica Status Solidi (A), Applied Research*, vol. 182, 2000, pp. 541-546.

(Continued)

*Primary Examiner* — Michael P Stafira
(74) *Attorney, Agent, or Firm* — Greer, Burns & Crain Ltd.

(57) ABSTRACT

The invention includes sensors and sensing methods for determining cell morphology and/or chemical composition of an analyte. A porous substrate exhibiting a first optical signal is exposed to a target analyte and subsequently monitored for changes in the optical signal. More specifically, a photonic or porous substrate having a well-defined and highly tunable reflectivity or transmission spectrum, such as porous silicon (Si), porous alumina, porous Ge, porous GaAs, porous SiO2 and porous polymer, is used for example. A porous or photonic substrate is exposed to an analyte, such as a cell or other macromolecule, and changes in the scattered light are observed over time to determine cell morphology and/or chemical composition of the analyte using the substrate.

21 Claims, 17 Drawing Sheets

U.S. PATENT DOCUMENTS

| | | | |
|---|---|---|---|
| 5,338,415 A | 8/1994 | Sailor | |
| 5,453,624 A | 9/1995 | Sailor et al. | |
| 6,248,539 B1 * | 6/2001 | Ghadiri et al. | 435/7.1 |
| 6,358,613 B1 | 3/2002 | Buriak | |
| 6,720,177 B2 | 4/2004 | Ghadiri | |
| 6,734,000 B2 | 5/2004 | Chin et al. | |
| 6,897,965 B2 | 5/2005 | Ghadiri et al. | |
| 7,042,570 B2 | 5/2006 | Sailor et al. | |
| 7,312,046 B2 | 12/2007 | Chin et al. | |
| 7,318,903 B2 | 1/2008 | Link et al. | |
| 2001/0044119 A1 | 11/2001 | Ghadiri et al. | |
| 2002/0072116 A1 | 6/2002 | Bhatia et al. | |
| 2002/0192680 A1 | 12/2002 | Chan et al. | |
| 2003/0146109 A1 | 8/2003 | Sailor et al. | |
| 2004/0152135 A1 | 8/2004 | Ghadiri et al. | |
| 2004/0171143 A1 | 9/2004 | Chin et al. | |
| 2004/0244889 A1 | 12/2004 | Sailor et al. | |
| 2005/0009374 A1 | 1/2005 | Gao et al. | |
| 2005/0019799 A1 | 1/2005 | Grasso et al. | |
| 2005/0042764 A1 | 2/2005 | Sailor et al. | |
| 2005/0101026 A1 | 5/2005 | Sailor et al. | |
| 2006/0051872 A1 | 3/2006 | Sailor et al. | |
| 2006/0105043 A1 | 5/2006 | Sailor | |
| 2006/0236436 A1 | 10/2006 | Li et al. | |
| 2006/0255008 A1 | 11/2006 | Link | |
| 2007/0051815 A1 | 3/2007 | Sailor et al. | |
| 2007/0108465 A1 | 5/2007 | Pacholski et al. | |
| 2007/0148695 A1 | 6/2007 | Sailor et al. | |
| 2008/0145513 A1 | 6/2008 | Li et al. | |
| 2008/0204752 A1 | 8/2008 | Dorvee et al. | |
| 2008/0212068 A1 | 9/2008 | Sailor | |

OTHER PUBLICATIONS

A. Janshoff et al., "Macroporous p-Type Silicon Fabry-Perot Layers. Fabrication, C haracterization, a nd A pplications i n B iosensing", *Journal o f American Chemical Society*, vol. 120, 1998, pp. 12108-12116.

Anderson, S.H.C. et al., "Dissolution of different forms of partially porous silicon wafers under simulated physiological conditions", *Phys. Stat. Sol.* (a), vol. 197, No. 2, 2003, pp. 331-335.

Bayliss, S.C. et al., "Phosphate and cell growth on nanostructured semiconductors", *Journal of Materials Science Letters*, vol. 16, 1997, pp. 737-740.

Bayliss, S.C. et al., "The Culture of Mammalian Cells on Nanostructured Silicon", *Advanced Materials*, vol. 11, No. 4, 1999, pp. 318-321.

Bayliss, S.C. et al., "The culture of neurons on silicon", *Sensors and Actuators*, vol. 74, 1999, pp. 139-142.

Bayliss, S.C. et al., "Nature of the Silicon-Animal Cell Interface", *Journal of Porous Materials*, vol. 7, 2000, pp. 191-195.

Berger, M.G. et al., "Dielectric filers made of PS: advanced performance by oxidation and new layer structures", *Thin Solid Films*, vol. 297, (1997) 237-240.

Canham, Leigh T. et al., "Derivatized Mesoporous Silicon with Dramatically Improved Stability in Simulated Human Blood Plasma", *Advanced Materials*, vol. 11, No. 18, 1999, pp. 1505-1507.

Chin, Vicki et al., "Compatibility of Primary Hepatocytes with Oxidized Nonporous Silicon", *Advanced Materials*, vol. 13, No. 24, Dec. 17, 2001, pp. 1877-1880.

Cunin, F. et al., "Biomolecular screening with encoded porous-silicon photonic crystals", *nature materials*, vol. 1, Sep. 2002, pp. 39-41.

Fink, Yoel et al., "A Dielectric Omnidirectional Reflector", *Science*, vol. 282, Nov. 27, 1998, pp. 1679-1682.

Foraker, Amy B. et al., "Microfabricated Porous Silicon Particles Enhance Paracellular Delivery of Insulin across Intestinal Caco-2 Cell Monolayers", *Pharmaceutical Research*, vol. 20, No. 1, Jan. 2003, pp. 110-116.

Hug, T.S. et al., "Optical waveguide lightmode spectroscopy as a new method to study adhesion of anchorage-dependent cells as an indicator of metabolic state", *Biosensors & Bioelectronics*, vol. 16, 2001, pp. 865-874.

Jay, T. et al., Autoclaving of Porous Silicon within a Hospital Environment: Potential Benefits and Problems, *Phys. Stat Sol.* (a), vol. 182, 2000, pp. 555-560.

Ji, Junmin et al., "Use of Microcontact Printing Methods to Direct Pattern Formation of Calcified Mesoporous Silicon", *Adv. Mater.*, vol. 14, No. 1, Jan. 4, 2002, pp. 41-43.

LaVan, David A. et al., "Small-scale systems for in vivo drug delivery", *Nature Biotechnology*, vol. 21, No. 10, Oct. 2003, pp. 1184-1191.

Li, Yang Yang et al., "Polymer Replicas of Photonic Porous Silicon for Sensing and Drug Delivery Applications", *SCIENCE*, vol. 299, Mar. 28, 2003, pp. 2045-2047.

Lord, Heather L. et al., "Development and Evaluation of a Solid-Phase Microextraction Probe for in Vivo Pharmacokinetic Studies", *Anal. Chem.*, vol. 75, No. 19, Oct. 1, 2003, pp. 5103-5115.

Mayne, A.H. et al., "Biologically Interfaced Porous Silicon Devices", *Physica* (a), vol. 182, No. 1, 2000, pp. 505-513.

Meade, Shawn O. et al., "Porous Silicon Photonic Crystals as Encoded Microcarriers", *Advanced Materials*, vol. 16, No. 20, Oct. 18, 2004, pp. 1811-1814.

Ostroff, Rachel et al., "Rapid multiserotype detection of human rhinoviruses on optically coated silicon surfaces", *Journal of Clinical Virology*, vol. 21, 2001, pp. 105-117.

Parrot, Sandrine et al., Microdialysis Monitoring of Catecholamines and Excitatory Amino Acids in the Rat and Mouse Brain: Recent Developments on Capillary Electrophoresis with Laser-Induced Fluorescence Detection—A Mini-Review, *Cellular and Molecular Neurobiology*, vol. 23 Nos. 4/5, Oct. 2003, pp. 793-804.

Ruiz-Hitzky, Eduardo, "Functionalizing Inorganic Solids: Towards Organic-Inorganic Nanostructured Materials for Intelligent and Bioinspired Systems", *The Chemical Record*, vol. 3, 2003, pp. 88-100.

Saito, Ryuta et al., "Distribution of Liposomes into Brain and Rat Brain Tumor Models by Convection-Enhanced Delivery Monitored with Magnetic Resonance Imaging", *Cancer Research*, vol. 64, Apr. 1, 2004, pp. 2572-2579.

Saleem, Azeem et al., "In vivo monitoring of drugs using radiotracer techniques", *Advanced Drug Delivery Reviews*, vol. 41, 2000, pp. 21-39.

Schmedake, Thomas A. et al., "Standoff Detection of Chemicals Using Porous Silicon 'Smart Dust' Particles", *Advanced Materials*, vol. 14, No. 18, Sep. 16, 2002, pp. 1270-1272.

Urbas, Augustine et al., "One-Dimensionally Periodic Dielectric Reflectors from Self-Assembled Block Copolymer-Homopolymer Blends", *Macromolecules*, 1999, vol. 32, 1999, pp. 4748-4750.

Wainwright, M. et al., "Morphological changes (including filamentation) in *Escherichia coli* grown under starvation conditions on silicon wafers and other surfaces", *Letters in Applied Microbiology*, vol. 29, 1999, pp. 224-227.

* cited by examiner

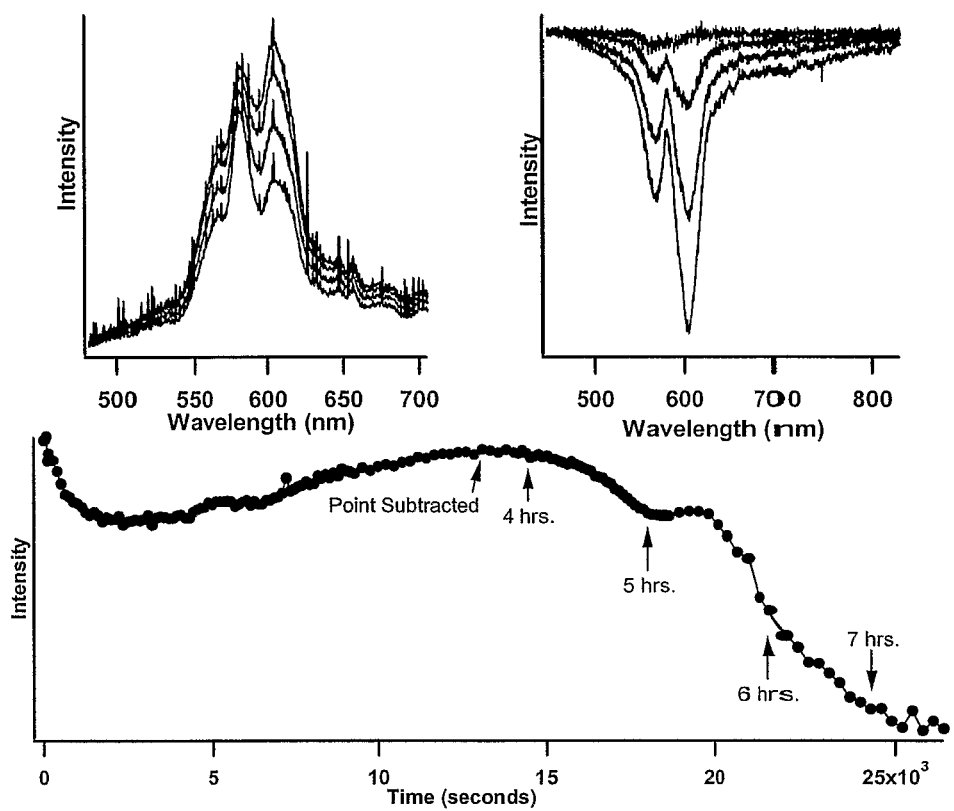
FIGs. 4a, 4b, 4c (left, right, bottom)

US 7,903,239 B2

POROUS PHOTONIC CRYSTAL WITH LIGHT SCATTERING DOMAINS AND METHODS OF SYNTHESIS AND USE THEREOF

PRIORITY CLAIM

Applicants claim priority benefits under 35 U.S.C. §119 on the basis of Patent Application No. 60/620,121, filed Oct. 19, 2004.

STATEMENT OF GOVERNMENT INTEREST

This invention was made with Government assistance under AFOSR Grant No. F49620-02-1-0288. The Government has certain rights in this invention.

TECHNICAL FIELD

The instant invention is directed to optical nanostructures, the synthesis of optical nanostructures, and the use of optical nanostructures in sensing applications.

BACKGROUND OF THE INVENTION

Detection, analysis and quantification of an analyte, such as a cell, macromolecule, protein, polymer, biomolecule, biopolymer or other molecular complex has widespread application in fields such as genomics, proteomics, drug discovery, medical diagnostics, environmental sensing, pollution monitoring, detection of chemical or biological warfare agents, and industrial process monitoring. For example, cell and tissue-based biosensors are useful for many medical, pharmaceutical, and environmental applications. One significant advantage of using living elements in sensors is that, in principle, complex biological interactions can be monitored. However, many biological events that signal changes in cellular physiology cannot readily be converted into an electronic signal in real-time.

Separately, silicon is commonly the primary constituent material of most common semiconductor chip circuitry, and as a consequence, there exists a widespread interest in silicon-based technology, such as silicon-based sensors. A form of silicon known as porous Si can be prepared from crystalline or polycrystalline silicon by chemical or electrochemical corrosion reactions. Pore size is readily tunable to correspond to a variety of biomolecules, and porous silicon chips that are biocompatible are easily produced using methods familiar to the semiconductor industry. As such, silicon is receiving increased attention for use with biomedical applications.

BRIEF SUMMARY OF THE INVENTION

The invention includes sensors and sensing methods whereby porous substrates exhibiting a first optical signal are exposed to a target analyte and subsequently monitored for changes in the optical signals. More specifically, the invention includes a photonic or porous substrate having a well-defined and highly tunable reflectivity or transmission spectrum, such as porous silicon (Si), porous alumina, porous Ge, porous GaAs, porous $SiO_2$ and porous polymer, for example. A porous or photonic substrate is exposed to an analyte, such as a cell or other macromolecule, and changes in the scattered light are observed over time to determine cell morphology and/or chemical composition of the analyte using the substrate.

DESCRIPTION OF THE DRAWINGS

FIG. 4a is a graph illustrating raw data for *Pseudomonas syringae* cells that have been infected with Φ6 virus;

FIG. 4b is a graph illustrating the indicated spectrum is subtracted from subsequent spectra;

FIG. 4c is a graph illustrating the intensity of the ~600 nm peaks over time;

BEST MODE FOR CARRYING OUT THE INVENTION

The invention exploits a scattering phenomenon whereby the intensity and/or the color of scattered light impinged on a porous or photonic substrate changes as a result of physiological changes in the cells overlaying the substrate. The intensity changes occur based on morphological changes in the cells that affect the efficiency of the scattering process. The color changes occur when substances, such as cells or molecules excreted by cells, enter the pores of the substrate. More specifically, the invention includes a porous or photonic substrate having a well-defined and highly tunable color, such as porous silicon (Si), porous alumina, porous Ge, porous GaAs, porous $SiO_2$ and porous polymer, for example. The porous substrate or cells seeded on a porous substrate are exposed to an analyte, a toxin, a virus, or other macromolecule that can affect cellular physiology, and changes in the scattered light are observed over time to determine cell morphology on and/or chemical composition in the substrate.

Figures 1A, 1B, 1C, 1D:
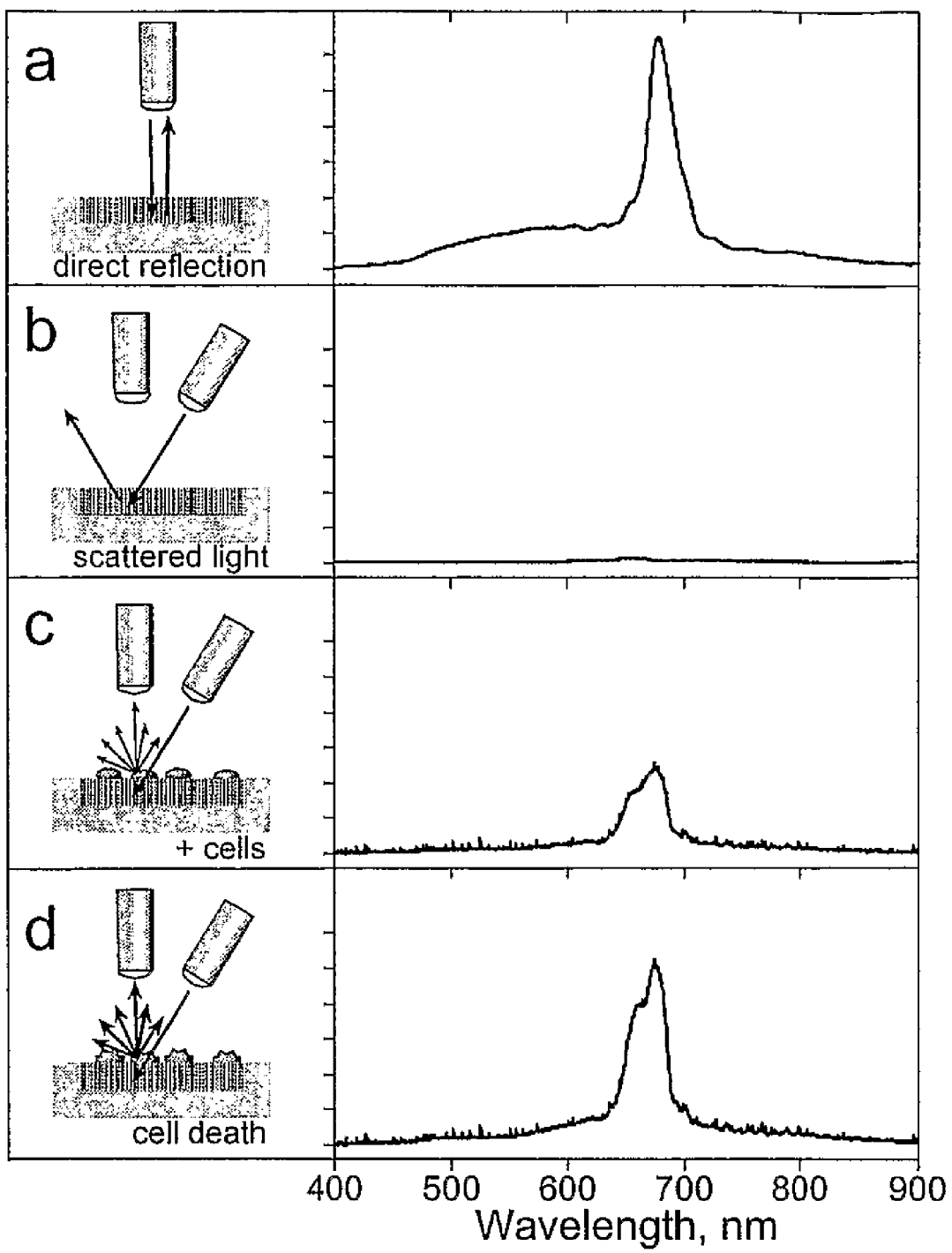
FIGS. 1a, 1b, 1c and 1d are graphs and schematic diagrams illustrating an optical design used to monitor biological events on a porous Si photonic crystal, with representative spectra, (a) along the axis normal to the chip surface, (b) incident from an off-normal position, (c) Placing cells on the surface of the chip introduces scattering centers that direct some of the specular reflection into the detection optics, (d) Changes in cell morphology alter scattering efficiency, which are detected as changes in intensity of the spectral peak.

For example, photonic crystals constructed from porous silicon (Si) include spectral properties, so called spectral "barcodes," such that when light impinges on the photonic crystals at an incident angle normal to a surface of the photonic crystals and is detected along the same axis, a characteristic sharp spectrum is observed (FIG. 1a). The intensity of a peak observed at normal incidence decreases rapidly when a light source is moved away from the surface normal, as illustrated in FIG. 1b. This rapid decrease in signal is due to a high specular reflectivity of the porous layer.

Light incident on the surface of the photonic crystal reflects specularly with very little scattering. However, when a defect that efficiently scatters light is present, as illustrated in FIG. 1c, the incident light is more efficiently scattered and can be collected with an appropriately positioned detector. Changes in the morphology of a scattering center lead to intensity changes in the off-specular scattered light, as illustrated in FIG. 1d. Thus, by measuring light scattered from a layer or multilayer of a porous Si film, it is possible to ascertain the presence and structure or physiology of analytes on the surface or within the pores of the porous Si film.

Accordingly, embodiments of the invention include biological and chemical sensors, as well as methods of synthesis and use of the biological and chemical sensors, wherein photonic crystals having a predetermined porosity gradient are exposed to a target analyte or a system suspected of containing the target analyte, and the spectral properties of photonic crystals having the analyte disposed on a surface thereof or within pores thereof are monitored and observed to determine the size, quantity, status, structure and/or morphology, and processes associated with the analyte.

More particularly, photonic crystals are preferably constructed from one of many porous substrates, such as, for example, porous Si, porous alumina, porous Ge, porous GaAs, porous $SiO_2$ and porous polymer. The photonic crystals or structures on the surface of the photonic crystal or structures embedded within the photonic crystal are exposed to analytes such as chemicals, cells, viruses, macromolecules, proteins, polymers, biomolecules, biopolymers, drugs, toxins, oligonucleotides (DNA or RNA) or other molecular complexes.

While it is contemplated that the invention encompasses a virtually unlimited array of biological and chemical sensing applications, several exemplary embodiments will be provided herein to demonstrate the principle of the invention.

A first preferred embodiment includes cell and tissue-based biosensors and biosensing methods, which are useful for many medical, pharmaceutical, and environmental applications. One significant advantage of using living elements in sensors and sensing applications is that, in principle, complex biological interactions can be monitored. However, many biological events that signal changes in cellular physiology cannot readily be converted into an electronic signal in real-time using previous methods. Scattering of light in the region in the immediate vicinity of the cell depends on the size, shape, and composition of the cell, and as such provides a highly localized probe of cell physiology In addition, the color of light scattered from the photonic crystal can depend on the concentration of species present in the porous Si matrix.

Accordingly, the first preferred embodiment provides biosensors and biosensing applications whereby continuous scattering measurements can detect the presence and quantity of cell, changes in cell morphology, cell mortality events and other cellular process in real time using simple optics, such as a white light source and a CCD spectrometer, a white light source and a digital imaging system, an LED and a photocell, a laser and a photodiode, or via visual inspection with a microscope or visual inspection with the naked eye. The invention has widespread applications, such as monitoring the presence of bacterial or mammalian cells, growth of bacterial or mammalian cells, viral infection of bacterial or mammalian cells, death of bacterial or mammalian cells due to toxic substances, the presence of cellular components such as lipids or excreted proteins or viruses, the attachment to and spreading of cells on the porous surface or modified porous surface, death of bacterial or mammalian cells due to the presence of toxic substances such as harmful drugs or other chemicals, or changes in mammalian or bacterial cell morphology due to the presence of toxic substances, viruses, hormones, or electrical stimuli. The response of multiple tissue samples to a drug or toxic substance may be monitored simultaneously, or multiple drug types may be sampled on a single group of cells or a combination of drug types and cell types may be simultaneously monitored. Further, modifications render embodiments of the invention suitable for sensing applications, such as monitoring biological agents in water or in air. While a virtually unlimited number of cells may be used in combination with the first preferred embodiment, two will be discussed in detail for purposes of illustration: 1) primary rat hepatocytes and 2) *Pseudomonas syringae* cells and Φ6 virus.

Preferably, a cell-based biosensor should employ a label-free technique that directly converts changes in cell physiology to a measurable signal in real-time. Porous silicon is an attractive substrate for cell-based biosensing since label-free detection and cell compatibility have been demonstrated with this material. Additionally, photonic structures with narrowband reflectivity spectra can be generated that can be used to encode small beads or specific regions of a chip for small-sample, highly parallel assays.

The spectrum of light scattered from an assembly of cells resident on a porous silicon photonic crystal provides a unique optical signature that is especially sensitive to changes in cell morphology. The scattering technique of the first preferred embodiment provides many advantages over current methods of signal transduction since measurements can be performed continuously on incubated cells without the use of on-chip sensors, modified or specialized cell-types, or fluorescent markers. It is anticipated that this method will have applications in basic mechanistic studies of cell morphology, sensing applications such as toxin, pathogen or microbe detection, as well as in cell-based high-throughput screening.

Two measurable effects exerted by the cells on the scattered light may be detected and correlated with an event on or within the porous Si film or within the immediate vicinity of the porous silicon surface. First, as previously illustrated in FIGS. 1a-1d, efficiency of scattering such that intensity of the light coupled from the optical film into free space is affected by changes in the cells' shape, size or refractive index. The second effect relates to the spectrum of the scattered light: if cells produce a species that can enter the pores of the porous Si film, the spectral distribution of the scattered light is modified because the index of refraction of the porous Si film is changed.

In the first preferred embodiment, the viability of cells, e.g., primary rat hepatocytes and *Pseudomonas syringae* cells, seeded on the surface of a porous Si photonic crystal is monitored. Light resonant with the photonic crystal is scattered by the cell monolayer and detected as an optical peak with a charge-coupled-device (CCD) spectrometer. Continuous scattering measurements can detect cell morphology changes that are precursors to toxin-induced (cadmium chloride or acetaminophen) cell death before decreases in viability are observed with traditional assays. The non-destructive scattering method thus represents a significant advantage for in-vitro, real-time monitoring of cell morphology.

Porous silicon may be generated by electrochemical etching of crystalline silicon in hydrofluoric acid solutions, and the porous silicon preferably includes a network of nanometer- to micron-scale pores separated by crystalline silicon domains. Under the appropriate conditions, one-dimensional photonic crystals can be fabricated from this material. The photonic crystals are formed by etching a periodic porosity gradient into the silicon wafer, resulting in a multilayer structure in which the refractive index of the layers varies between two or more values.

Example Using *Pseudomonas syringae* Cells and Φ6 Virus

First, a porous silicon film, preferably, but not limited to, a one-dimensional photonic crystal, is generated by electrochemical etching of crystalline silicon in hydrofluoric acid solutions, and includes a network of nanometer- to micron-scale pores separated by crystalline silicon domains. The photonic crystals are formed by etching a periodic porosity gradient into the silicon wafer, resulting in a multilayer structure in which the refractive index of the layers varies between two or more values. The surface of the porous silicon film is then chemically functionalized to specifically target a predetermined cell type or biomolecule. For example, in the instant embodiment, the porous silicon film is hydrosilylated to achieve a surface that is capped with a hydrocarbon chain and a carboxylic acid terminal group. In this case, the carboxylic group imparts compatibility with the cells to be studied. Different functional groups can be incorporated, including proteins, carbohydrates, or antibodies to impart specificity for a certain cell type or biomolecule. In a separate embodiment, coating and/or infiltration of the pores of the porous silicon layer with a polymer, one example being polystyrene, imparts on the porous silicon photonic crystal properties that are similar to a commercially available Petri dish, which is currently used for most cellular studies, but allows the optical properties to be preserved for monitoring purposes.

Next, the porous silicon film is submerged in growth medium, and the *Pseudomonas syringae* cells are allowed to grow for 24 hours. Growth was monitored in an incubator kept under optimal conditions until the observed reflectivity spectrum stopped changing. The method may optionally include agitation of cells while taking simultaneous reflectivity measurements, either through the use of mechanical agitation (such as with a stir bar) or aeration (such as by bubbling oxygen through the media).

Figure 2A:
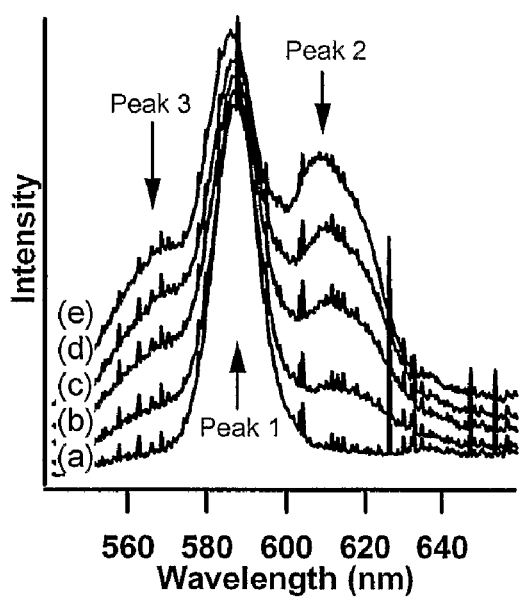
FIGS. 2a and 2b are graphs charting reflectivity spectra for the growth of *Pseudomonas syringae* bacteria.
Figure 2B:
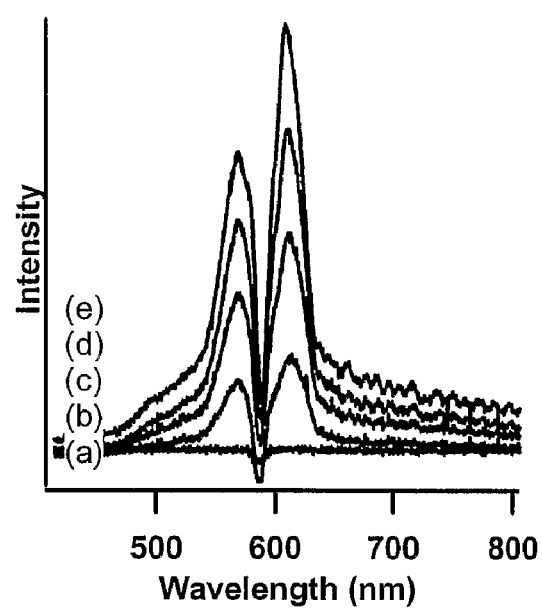
Figure 3:
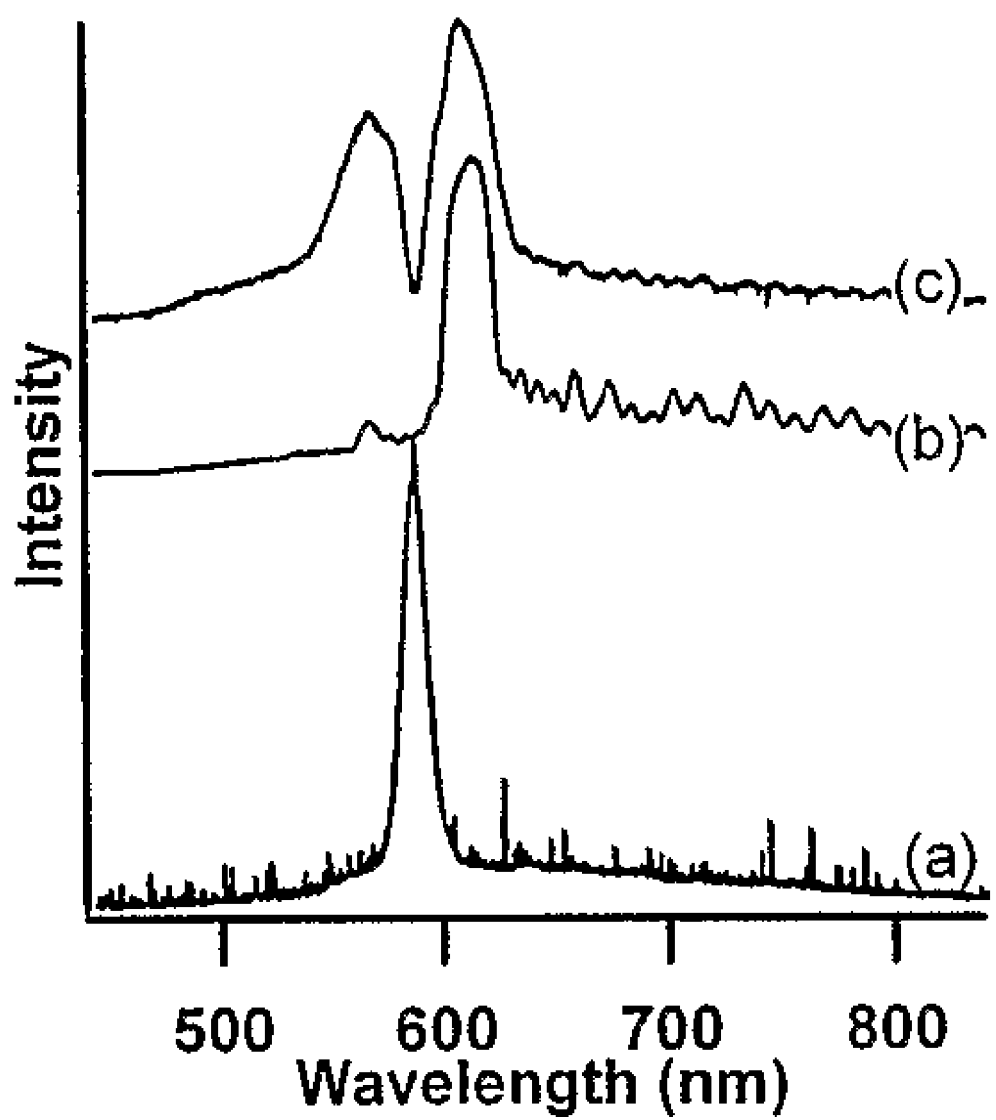
FIG. 3 is a graph illustrating (a) off-surface normal (off-axis) reflectivity spectrum for clean chip in media; (b) normal-axis (on-axis) reflectivity spectrum for clean chip in media; and (e) reflectivity spectrum after 22 hours of growth, with off-axis spectrum shown in (a) subtracted out.

The porous Si film and the cells disposed thereon are subjected to spectral analysis. FIGS. 2a and 2b illustrates off-axis reflectivity spectra for the growth of *Pseudomonas syringae* in a static solution, where only one peak (a) is present at the outset, whereas two peaks (b), (c) become apparent in the spectrum as the cells grow. Thus, spectrum (a) essentially represents a clean biosensor in media, whereas spectra (b) and (c) represent subsequent growth of the bacteria. The virus Φ6 is then added to the media, which infects the *Pseudomonas syringae* cells, reproduces, and causes the cells to burst and no longer contribute to scattering. As illustrated in FIG. 3, spectral analysis reveals that this results in a spectral decrease in intensity with time.

More specifically, FIG. 3 shows (a) the off-axis reflectance spectrum for the chip used for bacterial growth at time 0, (b) the on-axis reflectance spectrum for the same chip at time 0 (scaled to fit the figure), and (c) the corrected off-axis spectrum at the end of the growth phase (time=22 hrs.). The peak that is initially present for a clean biosensor remains constant, and can be subtracted out of subsequent spectra, and is therefore not present in the corrected spectrum in (c) of FIG. 3. The on-axis reflectance spectrum is characteristic of the etch conditions used for this particular experiment, and is typical for what is observed for porous silicon rugate structures. The two peaks that are observed in the corrected off-specular spectra are correlated to bacterial growth, as is illustrated in FIG. 2*b* and increase in intensity at the same rate. The peak at ~610 nm in (c) of FIG. 3 is almost identical to the specular reflection peak.

After a static growth phase was reached, Φ6 virus was added to the media. Φ6 virus infects *Pseudomonas syringae*, multiplies, which leads to bacteria cells that burst and therefore no longer contribute to scattering. FIGS. 4*a*-4*c* shows the raw spectra, corrected spectra, and a plot of peak intensity with time for *Pseudomonas syringae* infected with Φ6 (using the same bacterial cells that were monitored during the growth phase). The raw spectra plotted in the top, left in FIG. 4*a* represent the time points indicated on the plot of peak intensity vs. time (FIG. 4*c*). After reaching a maximum at about 4 hours, the peak intensity begins to decrease, corresponding to infected *Pseudomonas syringae* bursting. The initial decrease in intensity is due to temperature change as the sample is cooled by the incubator. However, the increase that is observed between ~1 and 4 hours, and the bump in intensity that is observed between 5 and 6 hours are reproducible features that are likely related to the infection process. The increases in scattering could be related to the process of virus reproduction within the bacterial cells, leading to an increase in scattering efficiency. Then, as cells begin to burst, they no longer contribute to the scattering signal and the peak intensity decreases. The bump in intensity between 5 and 6 hours is possibly due to a secondary infection phase. FIG. 4b shows difference spectra in which the spectrum at the point indicated was subtracted from the subsequent time points. As can clearly be observed, the intensity increases in the negative direction, indicating that peak intensity is decreasing for the two peaks that can be attributed to scattering. After completion of the experiment, the solution becomes visibly less turbid, indicating that bacteria cells have burst and are no longer acting as scattering centers.

Thus, precisely monitoring of the growth of bacteria and death of bacteria due to virus infection is possible. The ability to monitor the dynamics of bacterial infection in real time provides a potentially useful tool for biologists since time consuming plating experiments are not necessary. Furthermore, the use of standards should allow for the ability to quantify bacteria concentration using scattering intensity. The ability to precisely define the reflectivity peak by changing silicon processing conditions means that several experiments can be monitored at the same time, and therefore many different characteristics of cellular processes can be simultaneously determined. This could be especially useful since cells from the same batch could be monitored for several different conditions simultaneously, thereby leading to decreased inconsistencies due to the use of cells that have not been cultured at the same time.

Monitoring the peak position may provide information about cellular health and cell type or species. Because viruses can be specific and only able to infect specific bacterial cells, types or species, unique bacterial species could be identified if viruses specific to those unique cells were used. The ability to tailor the silicon surface to monitor for the presence of biomolecules can potentially make possible the ability to quantify virus concentration, leading to a significant potential tool for biologists. Since peak position is an indication of the refractive index of the porous silicon layer, the introduction of biomolecules changes the refractive index as the biomolecules replace media. Introduction of biomolecules therefore leads to measurable changes in peak position (which can be simultaneously monitored with peak intensity). The invention anticipates the ability to chemically functionalize the porous silicon surface to specifically target biomolecules. For example, probing for the presence of enzymes that are secreted by healthy cells or unhealthy cells would allow for monitoring of cellular health in real time. In the case of *Pseudomonas syringae*, targeting of Φ6 virus may allow for determination of virus concentration and allow for an additional parameter to be studied in conjunction with bacteria concentration. *Pseudomonas syringae* cells could also be targeted and distinguished from other bacteria that are resistant or immune to infections by Φ6. If cell burst is detected on the silicon surface in the presence of Φ6, then a bacterial species, such as *Pseudomonas syringae*, that is able to support Φ6 must be present. The absence of a burst indicates the absence of *Pseudomonas syringae* on the surface.

Example Using Primary Rat Hepatocytes

Porous silicon photonic crystal films can be formed in a variety of colors, and encoding of a potential one million codes has been demonstrated. Therefore, the ability to detect cell death for mammalian cells may provide a potential rapid drug screening technique since silicon processing technologies allow for small individual wells to be formed. Each well could contain a different cell type if screening for a particular drug is desired, or with the same cells if multiple drugs are to be screened. Changes in cell physiology for a particular well would be observable by changes in scattering intensity.

In the instant example, a porous silicon surface was modified using hydrosilylation chemistry. The hydrosilylated samples were then coated with a polystyrene layer to provide a surface similar to what is generally used for growth of mammalian cells.

One particular class of cells that is important for drug screening is hepatocytes. Since many drugs are metabolized by liver cells, it is important to screen for potential toxicity risks in order to prevent liver damage upon administration. Therefore, rat hepatocytes provide one exemplary model system for testing the potential for the porous silicon based assay.

Monitoring Living Cells

Turning again to FIGS. 1a through 1d, provided are schematic diagrams illustrating the optical design and representative spectra for the first preferred embodiment using the exemplary primary rate hepatocyte. The as-prepared porous Si photonic crystal immersed in culture media displays a reflectivity spectrum containing a sharp peak at a wavelength of ~650 nm when both the light source and the detector optics are positioned along the surface normal (optics perpendicular to the surface, as illustrated in FIG. 1a). If the incident light source is positioned off the surface normal, reflected light does not enter the acceptance cone of the detection optics (positioned normal to the surface, FIG. 1b) and the reflectivity peak is not detected by the spectrometer. The introduction of cells to the surface of the photonic crystal generates diffuse scattering, and some of the light incident on the wafer from the off-normal source is diverted into the detector (FIG. 1c). Changes in morphology of the scattering center affect the scattering efficiency and lead to changes in intensity of the observed peak (FIG. 1d).

Figures 5A, 5B, 5C:
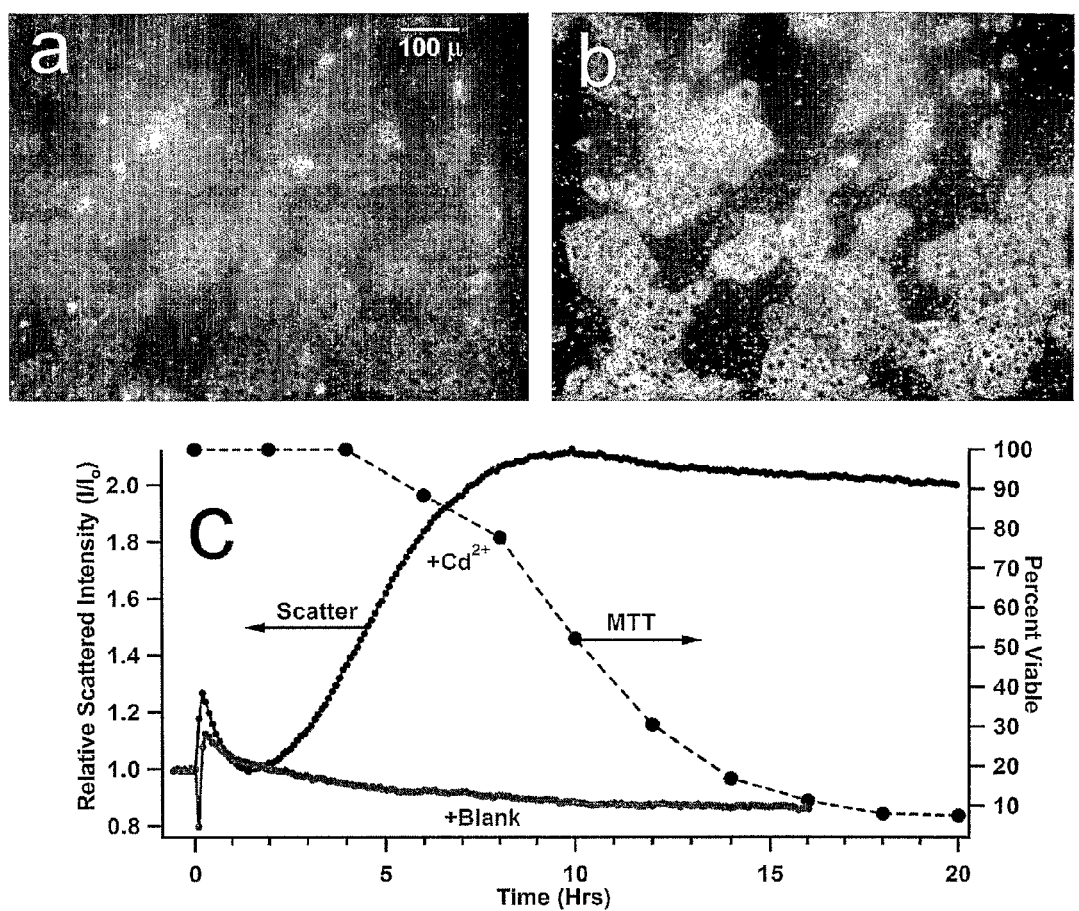
FIG. 5a is a microscope image of cells before exposure to $Cd^{2+}$ using an off-normal incidence white light source, where live cells appear with a color characteristic of the underlying photonic crystal, while the regions of the photonic crystal that are not covered with cells appear darker.
FIG. 5b is a microscope image of hepatocytes after exposure to 200 mM $Cd^{2+}$. Scattering efficiency increases as the hepatocytes lose viability, and cellular features such as nuclei can be easily resolved.
FIG. 5c is a graph illustrating plots of intensity of scattered light (left axis) and percent viability from MTT stain (right axis) as a function of time after introduction of 50 μM $Cd^{2+}$ to rat hepatocyte cells on a porous Si photonic crystal.
Figure 6:
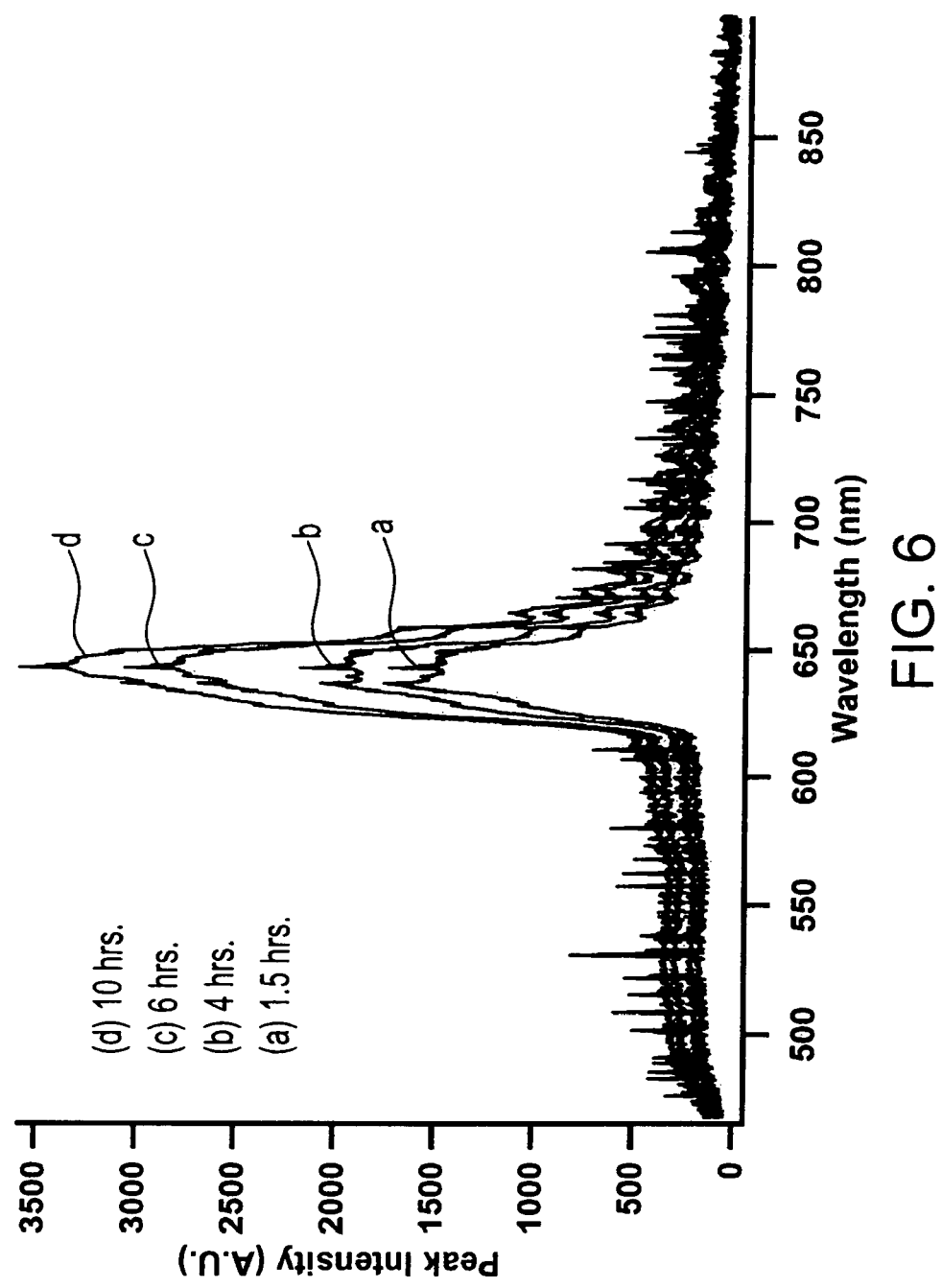
FIGS. 6a-6d are graphs illustrating representative reflectivity spectra used to generate the plots of I/Io vs. time in FIG. 1.
Figure 7:
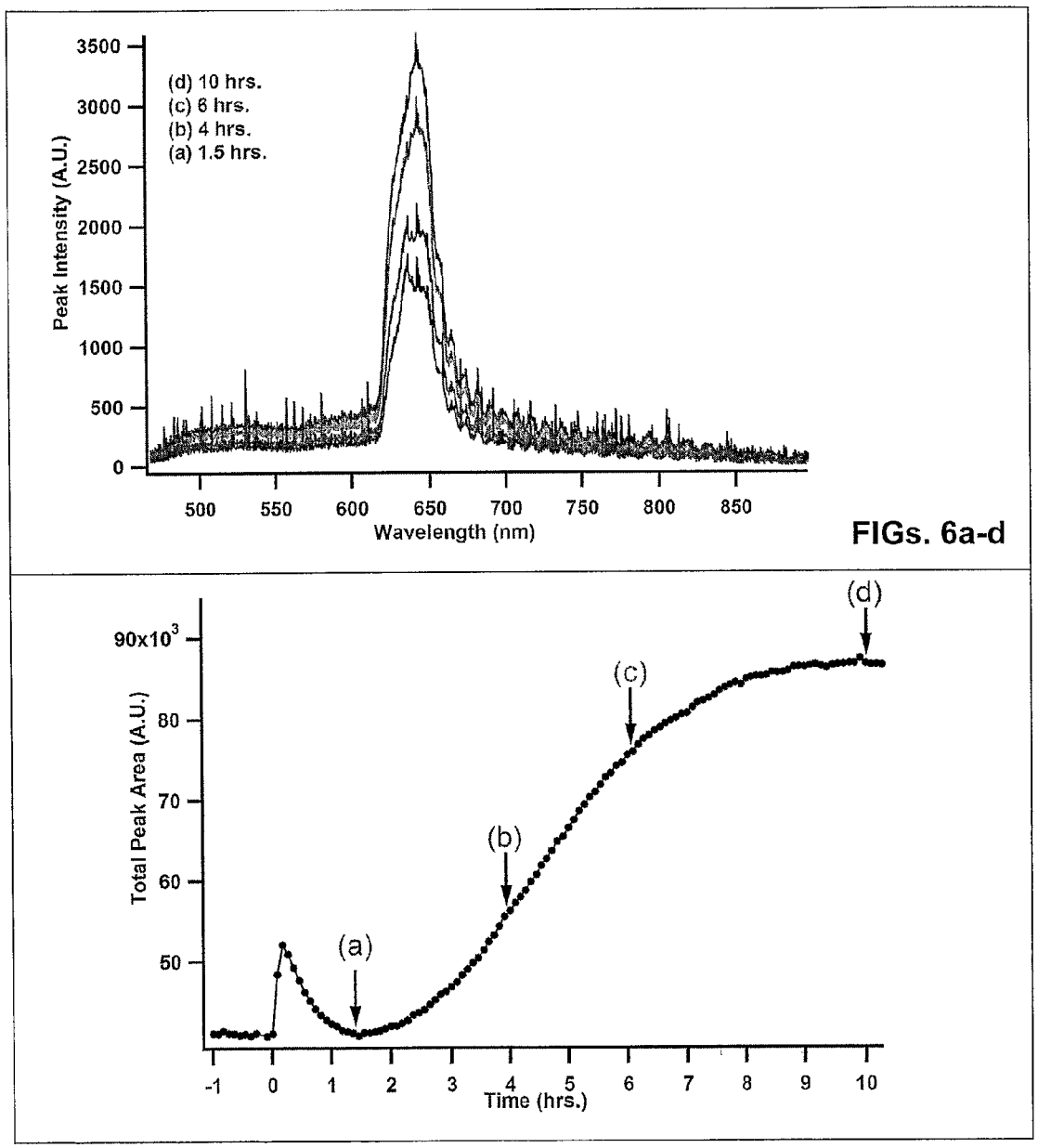
FIG. 7 is a graph illustrating a plot of integrated area of the scattered peak vs. time, where the times corresponding to the individual spectra in the top plot are indicated with the letters a-d.

While the first preferred embodiment contemplates use with a virtually unlimited variety of cell types, primary rat hepatocytes were chosen as an exemplary cell type to test the method due to the importance of hepatocytes in studies of drug metabolism. A plot of the change in scattered intensity vs. time for hepatocytes exposed to a toxic dose of cadmium chloride are presented in FIG. 5. Live cells appear with a color characteristic of the underlying photonic crystal, while the regions that are not covered with cells appear darker (FIG. 5a). Eighty-five min. after introduction of 200 μM $Cd^{2+}$, >90% of the hepatocytes have lost viability, and the cells in the images appear significantly brighter, with increased contrast in the nuclear and cell boundaries (FIG. 5b).

The changes in light scattering observed in the optical microscope can be quantified by spectroscopy. An important advantage of the spectroscopic measurement is that fiber optic cables can be used to interface an external illumination source and spectrometer with cells maintained in an incubator. Thus, hepatocytes seeded on a porous Si photonic crystal can be monitored in their ideal environment under controlled temperature and atmospheric conditions. The spot size used for the present experiments is on the order of 1 $mm^2$, which encompasses approximately 500 hepatocyte cells.

FIG. 5c shows plots of relative intensity of scattered light vs. time for hepatocytes seeded on a porous Si photonic crystal that have been exposed to 50 μM $Cd^{2+}$ ("+$Cd^{2+}$") and 0 μM $Cd^{2+}$ ("+Blank"). Representative raw spectra are presented in FIGS. 6a-6d and 7. Cell viability after exposure to 50 μM $Cd^{2+}$ was monitored in parallel experiments using a conventional MTT (Methylthiazolyldiphenyl-tetrazolium bromide) stain (FIG. 5c, "MTT stain;" solid circles). For both samples monitored spectroscopically, addition of solution ($Cd^{2+}$ or blank media) produces an initial spike in peak intensity, attributed to condensation effects caused by opening the incubator. However, while scattering intensity for the control returns to baseline after condensation dissipates, the sample in which hepatocytes are exposed to $Cd^{2+}$ shows a significant increase in relative intensity after ~2 h. The changes in scattering intensity after hepatocytes are exposed to 50 μM $Cd^{2+}$ correlate to observed physical changes using phase-contrast microscopy, and occur ~2 h before the MTT stain begins to indicate loss of viability. The intensity of scattered light reaches a constant value after ~10 h, while viability according to the MTT stain only decreases to ~50% of the initial value in the same time period. Scattered light intensity stabilizes before the MTT stain indicates complete loss of viability, indicating that this method detects morphology changes that are precursors to cell death.

Several morphological changes that are considered precursors to loss of cellular viability might lead to the increase in light scattering observed in the present example, including changes in mitochondrial composition and lipid formation. The phenomenon of $Cd^{2+}$-induced toxicity in hepatocytes has been widely studied; the primary cause for loss of viability is generally attributed to interruption of metabolic activity. Cell damage due to concentrations of $Cd^{2+}$ in the 50-400 μM range occurs within the first hour of exposure, and includes a decrease in membrane and metabolic integrity. Measures of metabolic function and membrane integrity are more sensitive indicators of early $Cd^{2+}$-induced cytotoxicity than the MTT assay, and the timescale in which scattering changes occur due to a toxic dose of $Cd^{2+}$ coincides with the timescale reported for these tests. However, while most other techniques require sampling of media or addition of dyes, light scattering can be continuously observed while the cells remain incubated and undisturbed.

Figure 8:
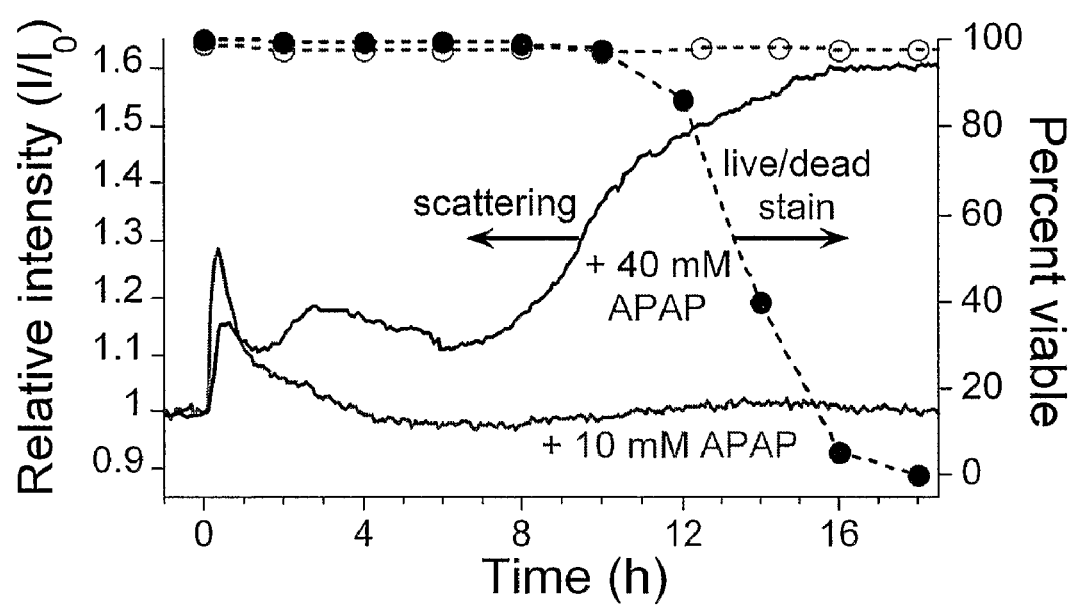
FIG. 8 is a graph monitoring acetaminophen (APAP)-induced morphology changes in rat hepatocytes by light scattering from a photonic crystal substrate.

FIG. 8 presents light scattering and viability data for hepatocytes exposed to sub-toxic and toxic doses (10 and 40 mM, respectively) of acetaminophen (N-acetyl-p-aminophenol, or APAP). The light scattering results for hepatocytes on a porous Si photonic crystal are compared to the ethidium live/dead assay on cells seeded on tissue-culture polystyrene. After introduction of 10 mM APAP (FIG. 2, "+10 mM APAP"), a spike in scattering intensity due to condensation effects is followed by a return to baseline, indicating that this dose is not toxic to hepatocytes within the time scale of the experiment. The live/dead assay (FIG. 8, open circles) and phase-contrast microscope images confirm that a 10 mM dose of APAP is sub-toxic and does not cause a loss of hepatocyte viability. By contrast, exposure to 40 mM APAP results in a significant increase in scattered intensity within ~3 h of addition, with the largest intensity change beginning after ~8 h (FIG. 8, "+40 mM APAP"). The live/dead stain indicates that all cells lose viability within ~19 h of introduction of 40 mM APAP, with the first signs of cell death occurring after ~12 h (FIG. 8, solid circles). Signs of cellular stress within the first few hours of introduction of 40 mM APAP are also observed using phase-contrast microscopy. Similar to the $Cd^{2+}$-exposure results (FIG. 5), light scattering from a porous silicon photonic crystal indicates changes in cell morphology well before loss of viability is observed using the live/dead assay.

The light scattering results for hepatocytes on chips exposed to 40 mM APAP are similar, but not identical, to those observed for $Cd^{2+}$ exposure. The mechanism for APAP-induced toxicity differs from $Cd^{2+}$ in that APAP does not directly cause cell damage. Rather, APAP is metabolized to form N-acetyl-p-benzoquinone (NAPQI), which then covalently binds proteins and interrupts cellular function. APAP toxicity occurs in two distinct phases, a metabolic phase and an oxidative phase, with the first signs of cell lysis or leakage occurring after ~2 h. Distinct changes in mitochondrial permeability have been observed for hepatocytes exposed to toxic doses of APAP, with the first occurring 3-6 h and the second 9-16 h after administration. In the present example, the light scattering data reproducibly display a feature ~2-6 h after APAP introduction (FIG. 8, "+40 mM APAP"), which may be attributable to cell morphology changes induced by the metabolic phase of APAP toxicity. The difference in the time-dependent scattering changes observed for the different toxins (acetaminophen and $Cd^{2+}$) indicates that this method provides information useful for detailed mechanistic studies of cell viability.

The changes in intensity of a spectral band scattered from an assembly of cells on a one-dimensional porous Si photonic crystal detects cellular morphology changes that are precursors to loss of viability several hours in advance of conventional viability staining methods. In this example, the light scattering method is used to detect changes in morphology of rat hepatocyte cells, though the method can be generalized to any biological entity that is large enough to scatter light. One of the primary advantages of the porous Si-based system is that the monitoring apparatus can be incorporated into an incubator or integrated with a conventional light microscope equipped with an inexpensive CCD spectrometer. The porous Si photonic crystal on which the cells reside provides a surface similar to a standard Petri dish, although more complex biosensing schemes could be envisioned in which recognition elements are incorporated in the film to monitor specific cellular byproducts. An additional advantage to using porous Si-based photonic crystals is that the materials can be prepared with >$10^6$ spectral "barcodes," enabling multiplexing of cellular libraries for high-throughput screening applications. The scattering method reported here represents a label-free, non invasive method to continuously monitor cell morphology, important to many areas of biotechnology.

Exemplary methodology associated with the monitoring of living cells follows. Briefly, 1-dimensional photonic crystals of porous silicon that display a single spectral reflectivity peak were prepared and filled with polystyrene by solution-casting to provide a surface coating similar to a conventional Petri dish. Hepatocytes were isolated from 2-3 month old adult female Lewis rats by collagenase perfusion as previously described. Hepatocytes were then seeded on the polystyrene-coated porous silicon samples or on tissue-culture polystyrene dishes.

Figures 9A, 9B:
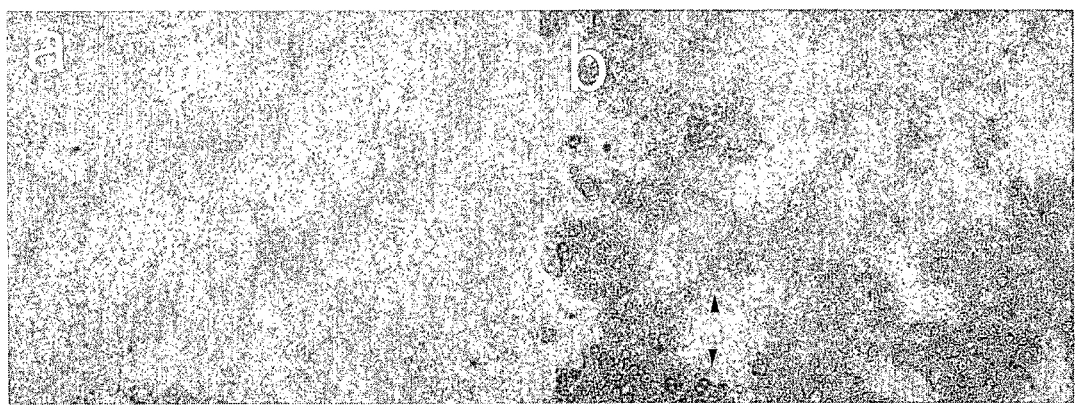
FIGS. 9a and 9b are reflectance optical microscope images of rat hepatocyte cells on the surface of a porous Si photonic crystal, with (a) live and (b) dead cells, obtained with the illumination source and observation axis coincident with the surface normal to the chip.
Figures 10A, 10B, 10C, 10D:
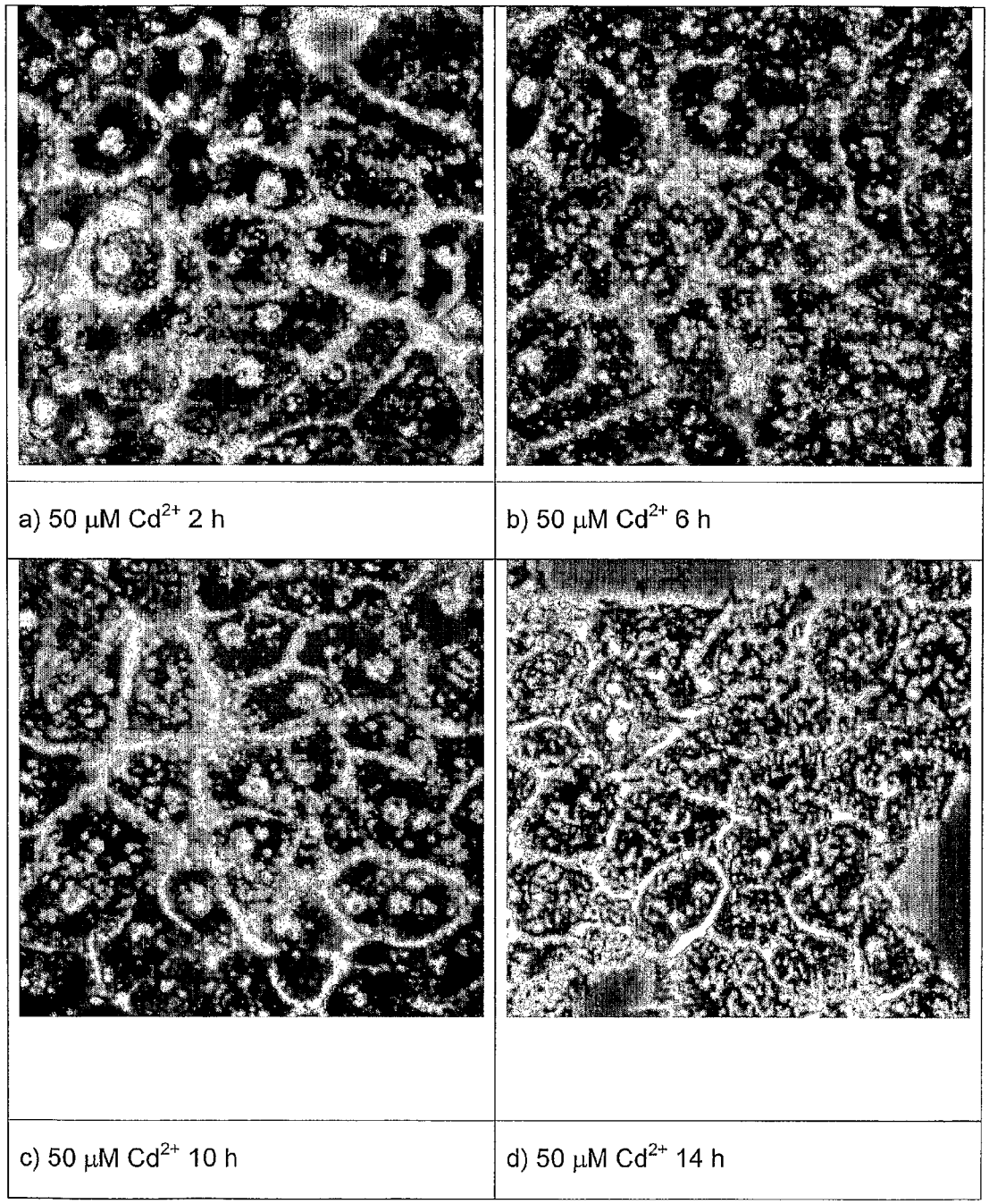
FIGS. 10a-10d illustrate phase-contrast microscope images for primary rat hepatocytes seeded on tissue-culture polystyrene plates after exposure to 50 mM $Cd^{2+}$ at (a) 2 h, (b) 6 h, (c) 10 h, and (d) 14 h.
Figures 11A, 11B, 11C, 11D:
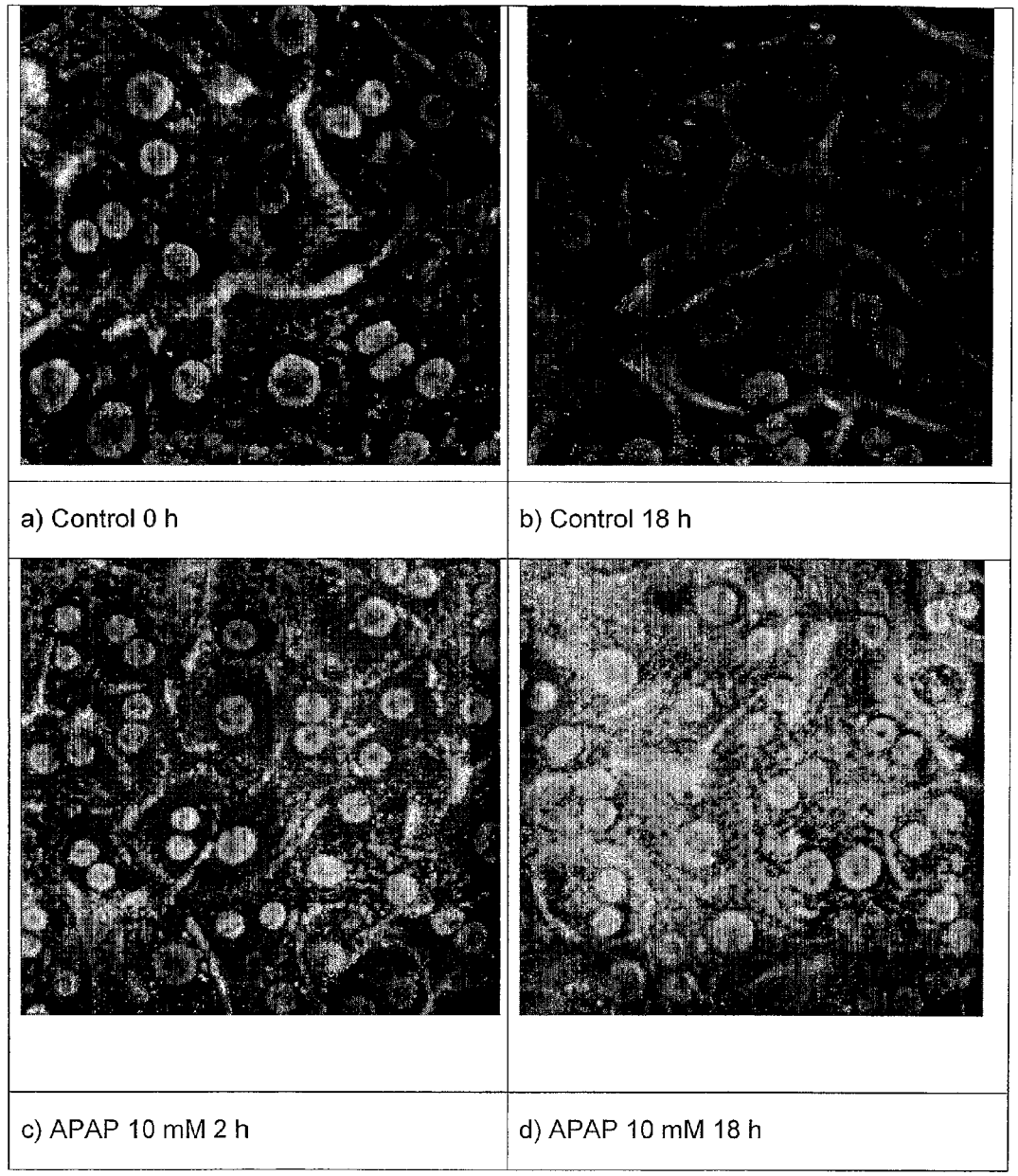
FIGS. 11a-11d illustrate phase-contrast microscope images for control experiments: (a) Hepatocytes at t=0. (b) Hepatocytes without toxin after 18 h. (c) Hepatocytes exposed to 10 mM APAP after 2 h. (d) Hepatocytes exposed to 10 mM APAP after 18 h.
Figures 12A, 12B, 12C, 12D:
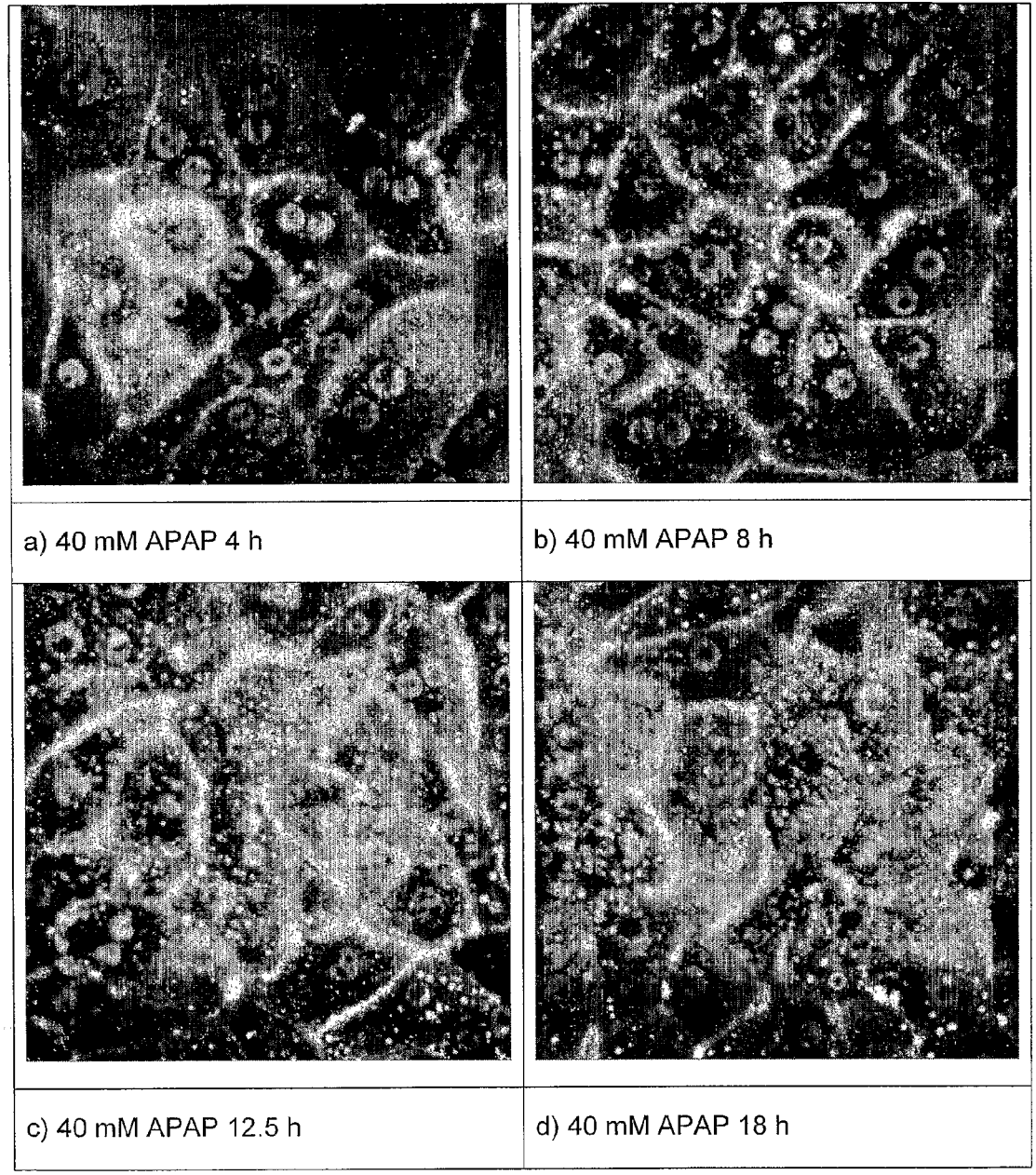
FIGS. 12a-12d illustrate phase-contrast microscope images of primary rat hepatocytes seeded on tissue-culture polystyrene plates after exposure to 40 mM N-acetyl-p-aminophenol (APAP) at (a) t=4 h, (b) 8 h, (c) 12.5 h, and (d) 18 h.

More particularly, measurement of light scattered from a monolayer of hepatocyte cells on a porous Si photonic crystal is used to measure changes in cellular morphology. Data were collected after hepatocytes were administered a toxic dose of aqueous cadmium chloride (200 μM). In order to follow the same subset of cells throughout the course of morphology changes, the cells were not incubated in this experiment, and they were administered a larger dose of $Cd^{2+}$ than was used in the in-situ incubator experiments (200 μM vs. 50 μM, respectively). Before exposure to $Cd^{2+}$, reflectance light microscopy reveals that individual cells are somewhat difficult to resolve on the photonic crystal substrate (FIG. 9a). Upon exposure to $Cd^{2+}$, characteristic changes in morphology that accompany loss of viability, such as blebbing and increased granularity, are observed (FIG. 9b). The optical setup produces more dramatic images upon exposure to a toxic dose of $Cd^{2+}$. In this arrangement, cells appear with a color characteristic of the underlying photonic crystal, while the regions that are not covered with cells appear darker (FIG. 5a). After loss of viability, the cytoplasm appears brighter, leading to greater nuclear and cell boundary contrast (FIG. 5b). Membrane blebbing does not appear to contribute to an increase in light scattering.

FIGS. 10a-10d illustrate images that were taken to present phase-contrast microscope images in which primary rat hepatocytes seeded on tissue-culture polystyrene plates are monitored. The images of reveal very distinct changes in morphology after hepatocytes are exposed to 50 μM $Cd^{2+}$. In particular, granular appearance increases substantially, even after 2 h. Apparent lipid droplet formation is evident after 2 h (circular, phase-bright features), which either disappears or is obscured by other morphological changes at later times. By 14 h, most cellular features become indistinguishable. The immediate appearance of granularity (and possibly lipid droplets) after exposure to $Cd^{2+}$ correlates with the changes in scattering intensity.

As illustrated in FIGS. 11a-11d, images were also obtained for control experiments in which primary rat hepatocytes seeded on tissue-culture polystyrene plates are monitored using a phase-contrast microscope. Hepatocytes remain healthy and relatively unchanged after 18 h, either without (a-b) or with (c-d) the addition of 10 mM N-acetyl-p-aminophenol (APAP).

Images illustrated in FIGS. 12a-12d indicate that exposure to a toxic dose of APAP leads to very different morphology changes compared to $Cd^{2+}$. In particular, lipid droplets (circular, phase-bright features) are observed starting at 2 h, with the frequency of these features increasing for each time point. By 12 h, hepatocytes exposed to APAP begin to show significant granular appearance, similar to what is observed for $Cd^{2+}$. There is a clear qualitative correlation to the scattering data for physical changes for hepatocytes exposed to toxic doses of APAP and $Cd^{2+}$.

Figures 13A, 13B:
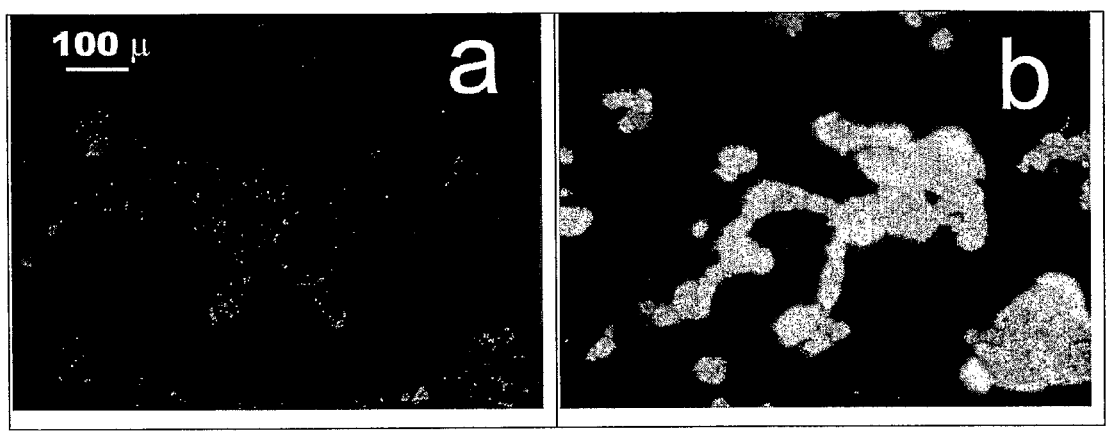
FIGS. 13a and 13b illustrate reflectance microscope images monitoring morphology changes for hepatocytes exposed to APAP, where images were collected (a) before and (b) 20 h after addition of 40 mM acetaminophen.

As illustrated in FIGS. 13a and 13b, images obtained present a comparison of microscope images for hepatocytes (a) before and (b) 20 h after exposure to 40 mM N-acetyl-p-aminophenol (APAP). Cells appear with a color characteristic of the underlying photonic crystal, while the regions of the photonic crystal that are not covered with cells appear dark. After the cells lose viability due to exposure to APAP, they appear much brighter in the scattered light images. To visually demonstrate the potential for encoding cells on different regions of a chip using the photonic properties of the porous Si substrate, the photonic crystal used for the APAP experiment was etched such that the reflectance peak appeared in the green region of the spectrum. In contrast, the cells exposed to $Cd^{2+}$ were seeded on a red chip.

Preparation of porous silicon photonic crystals. Samples of one-dimensional photonic crystals of porous silicon displaying a single spectral peak were prepared and the pores were filled with polystyrene by solution-casting to provide a surface coating similar to the surface of conventional petri dishes. Porous Si samples were prepared from single-crystal, highly doped p-type silicon (boron doped, 0.0005-0.0015 Ω-cm resistivity, polished on the (100) face) by electrochemical etch in a 3:1 solution of 49% aqueous hydrofluoric acid: ethanol. Samples were etched using a computer-generated sinusoidal waveform with current density ranging from 13-66 $mA/cm^2$ and a period of 4-7 s (depending on the exact resistivity of the wafer and the color desired) for 75 cycles, producing a porous film of ~30 μm in thickness on the Si substrate. The samples were then placed in neat undecylenic acid (98%) and heated to 140° C. for 2 hours, resulting in a covalently bound hydrocarbon layer terminated with a carboxylic acid group. The undecylenic acid coating was found to improve the adhesion of the polystyrene coating and also to increase stability of the chip towards corrosion in cell media. To coat the porous film with a uniform polymer layer, a solution of 30% (by wt.) polystyrene (45,000 average M.W.) in toluene was spin-coated on the undecylenic acid-terminated surface, and heated to 180° C. in an oven for 30 minutes. The polystyrene-coated surface was activated by exposure to a 200 W $O_2$ plasma for 1 min. to provide a hydrophilic substrate that promoted cell adhesion. Hepatocytes were then seeded on the activated polystyrene-coated chip.

Cell seeding. Porous Si photonic crystal samples were sterilized in a 35 mm dish with 2 mL of 100% ethanol for 1 hour. Ethanol was removed and the samples were allowed to dry in a sterile laminar-flow hood. The samples and dish were washed twice with sterile water. To improve adhesion, 2 mL of a 0.1 mg/mL solution of rat-tail collagen (collagen I) was added to the dish, and the samples were incubated at 37° C. for one h. The collagen-coated samples were then washed once with sterile water, and once with growth media. Media for all experiments was DMEM with high glucose (Invitrogen), 10% fetal bovine serum, supplemented with 0.5 U/mL insulin, 7 ng/mL glucagon, 7.5 mg/mL hydrocortisone, 10 U/mL penicillin, and 10 mg/mL streptomycin. Hepatocytes were isolated from 2-3 month old adult female Lewis rats by collagenase perfusion as previously described. Less than one hour after isolation, $1.25 \times 10^6$ cells per dish were seeded in 2 mL of media for scattering experiments and $6 \times 10^5$ cells per dish for microscope experiments. As the porous Si samples were smaller than the dish, some cells settled and attached to the polystyrene surface. Unattached cells were removed after one hour and dishes were incubated at 37° C., 5% $CO_2$ for 24 hours to allow spreading before the start of observation.

Cell viability assays. Cell viability assays were performed in 6 well plates (BD/Falcon). The procedure for seeding cells was the same as for porous silicon samples except for the seeding concentration, which was $5 \times 10^5$ cells per well. For live/dead staining, samples were incubated with Ethidium Homodimer and Hoechst 33258 for 30 minutes and examined by fluorescence microscopy. Cultures of hepatocytes assayed for cell viability with MTT (Methylthiazolyldiphenyl-tetrazolium bromide or Thiazolyl Blue Tetrazolium Bromide) were washed with sterile PBS (phosphate buffered saline solution) and a solution of 0.5 mg/mL MTT in DMEM without phenol red was added. After one hour at 37° C., the media was removed and the purple precipitate was dissolved in 50% DMSO/isopropanol. The intensity of the purple color was measured as the absorbance at 570 nm minus background at 660 nm. Viability was determined by comparison to control cultures with no exposure to toxin.

Optical measurements. Images for cells seeded on porous silicon photonic crystals were collected using a reflectance microscope and a 10x LWD objective with on-normal and off-normal illumination using a white light source. Phase contrast images for cells seeded on tissue cultured polystyrene multi-well plates were obtained on a Nikon TE200 microscope with a 10x objective and captured with a camera. Images were processed on Metamorph and JImage. Images were monitored by optical microscopy to demonstrate the types of changes that can be observed using a porous silicon photonic crystal. Cells were seeded on the porous Si chips at less than 100% coverage so that the porous silicon background could provide contrast. In order to follow the same subset of cells throughout the course of morphology changes for the $Cd^{2+}$ toxicity studies, the cells were not incubated while monitoring with the microscope. Rather, cells were placed on a chip and $Cd^{2+}$ concentration was adjusted to a final concentration of 200 μM. Pictures were obtained at time 0 and 85 minutes.

Reflectance spectra were collected using an Ocean Optics S-2000 CCD spectrometer fitted with a microscope objective lens coupled to either a bifurcated fiber optic cable (for specular measurements) or a single fiber optic cable (for scattering measurements). A tungsten light source was focused onto the center of the porous silicon photonic crystal surface with a spot size of approximately 1 $mm^2$, either through the same optics used by the spectrometer (normal reflection mode) or via separate optics (scattering mode). Reflectivity data were recorded in the wavelength range of 400-1000 nm, with a spectral acquisition time of 500-2000 ms (depending on the quality of the photonic structure). Typically 20-100 spectral scans (up to 50 s total integration time) were averaged per time point. Data points were collected every 300 s.

Data analysis. The wavelength axis of the spectrum from the Ocean Optics spectrometer was calibrated using a least-squares fit of five spectral lines observed from a neon lamp, at 585.3, 614.3, 640.2, 703.2, and 811.5 nm. The data spacing is approximately 0.4 nm. The intensity of the spectral peak was quantified as the total integrated area of the peak by trapezoidal integration. For the data presented in FIGS. 6a and 6b, the scattering peak was integrated between 615 and 680 nm. The relative scattered peak intensity ($I/I_o$) is defined as the ratio of the integrated peak intensity at a given time to the integrated peak intensity at time t=0, with t=0 being defined as the time immediately before addition of toxin (or media blanks in the case of the controls).

A second preferred embodiment of the invention includes sensors and sensing methods whereby pores of a photonic crystal are impregnated with a molecular species and scattered light spectra are measured over time to monitor the release of the molecular species from the pores of the photonic crystals. The molecular species deposited into the pores, such as soluble species by impregnation from solution, form aggregates that act as scattering centers, distributing light from the resonant optical structure over a large solid angle. The spectrum of the scattered light displays features whose wavelength and intensity are dependent on the amount of material loaded into the pores, providing a convenience means of monitoring the temporal release characteristics of the material. An application of the second preferred embodiment include, for example, release of a drug into aqueous solution from a porous Si photonic crystal. Potential applications therefore include controlling and monitoring temporal release of a drug, both in vivo and in vitro.

While it is contemplated that the invention could be used with any of a vast array of molecular species, for purposes of illustration, the examples of polystyrene, caffeine and dexamethasone will be discussed.

Polystyrene Example

Porous Si sample containing small domains of polystyrene demonstrate the resonant scattering phenomenon. A 1-dimensional photonic crystal is provided that displays a sharp resonance in the reflectivity spectrum. A fine mist of a solution of polystyrene in toluene is then impinged on the surface by spray-coating, such as with a commercial artist's air brush. The sample is then heated in an oven at 110° C. for 15 min to infuse the polymer into the porous matrix. The resulting structure contains a multitude of polystyrene domains of less than 1 mm in diameter, dispersed in the porous Si film.

Figure 14:
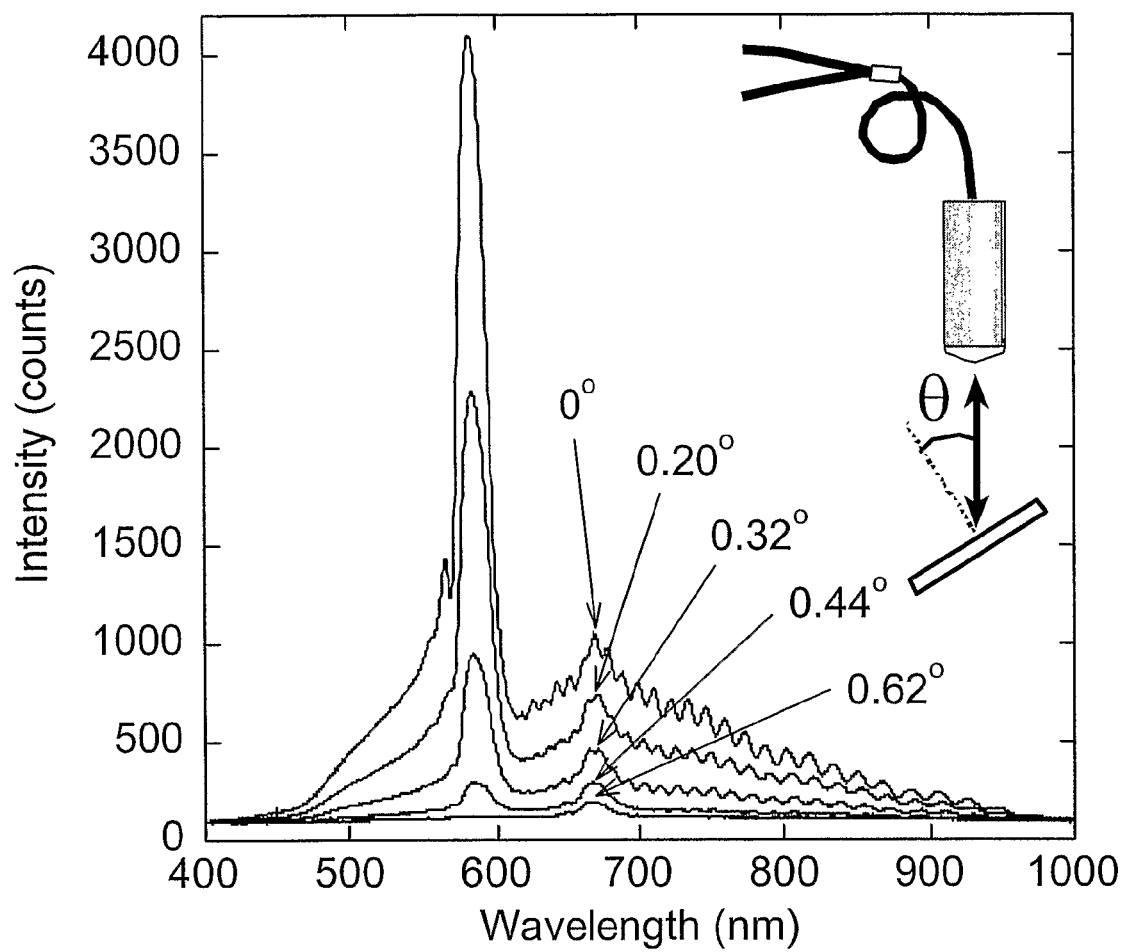
FIG. 14 is a graph illustrating spectra obtained from a porous Si photonic crystal sample coated with polymer dots, as a function of angle.

The rugate peak in the spectrum of the sample splits into two peaks upon infusion of the polymer (FIG. 14). A peak at 580 nm is associated with regions of the photonic crystal without polymer, and a peak at 670 nm corresponds to the polymer-infused regions. The spectrum from the polymer-infused material is red-shifted due to the larger refractive index of polystyrene relative to air. The scattering phenomenon is clearly apparent in the angle dependence of the intensities of these two peaks. A bifurcated fiber optic cable and lens assembly can be used to obtain spectra from the sample as a function of angle. In this setup, the axis of observation is coincident with the axis of illumination, and the angle q between this axis and the vector normal to the surface of the sample is varied (FIG. 14 inset). As the angle q increases from 0°, the specular reflection peak at 580 nm rapidly decreases in intensity. The intensity of the peak at 670 nm, corresponding to light resonant in the polymer domain, decreases much more slowly. The angle dependence of the 670 nm feature is consistent with scattered rather than specularly reflected light. As the polystyrene or other drug is released from the porous matrix into a solution, changes in scattering can be used to monitor the rate of release of the drug from the porous matrix into solution.

Caffeine Example

As with a metallic mirror, the intensity of light reflected from a one-dimensional photonic crystal falls to zero very quickly if the position of observation is not along the specular reflection axis. Microdomains of certain polymers, liquids, or solids can be generated in 1-dimensional photonic crystals of porous Si, and these structures scatter light resonant in the photonic crystal over a large solid angle. Use of the phenomenon in an application involving remote monitoring of drug delivery is demonstrated.

Scattering from domains of the small molecule drugs dexamethasone and caffeine in the porous Si matrix is readily observed by eye, demonstrating an application of the phenomenon relevant to drug delivery. Rigid micro- and mesoporous solids are of great interest as reservoir-based drug delivery materials, and since porous Si in particular has a demonstrated biocompatibility and biodegradability in vitro and in vivo, porous Si has been under intensive investigation for controlled release and other biomedical applications.

In many cases, in vivo monitoring of the release characteristics of a particular drug is needed. Methods based on magnetic resonance imaging, solid-phase microextraction, microdialysis, and labeling with fluorescent or radioactive tracers have been developed. The resonance feature from a photonic crystal can also be used to monitor drug release, when the material is prepared with spectral peaks at near infrared, tissue-penetrating wavelengths. The scattering phenomenon described in this example provides a means to improve the ability to monitor such fixtures through human tissue, especially as the size of these devices becomes smaller.

Figures 15A, 15B:
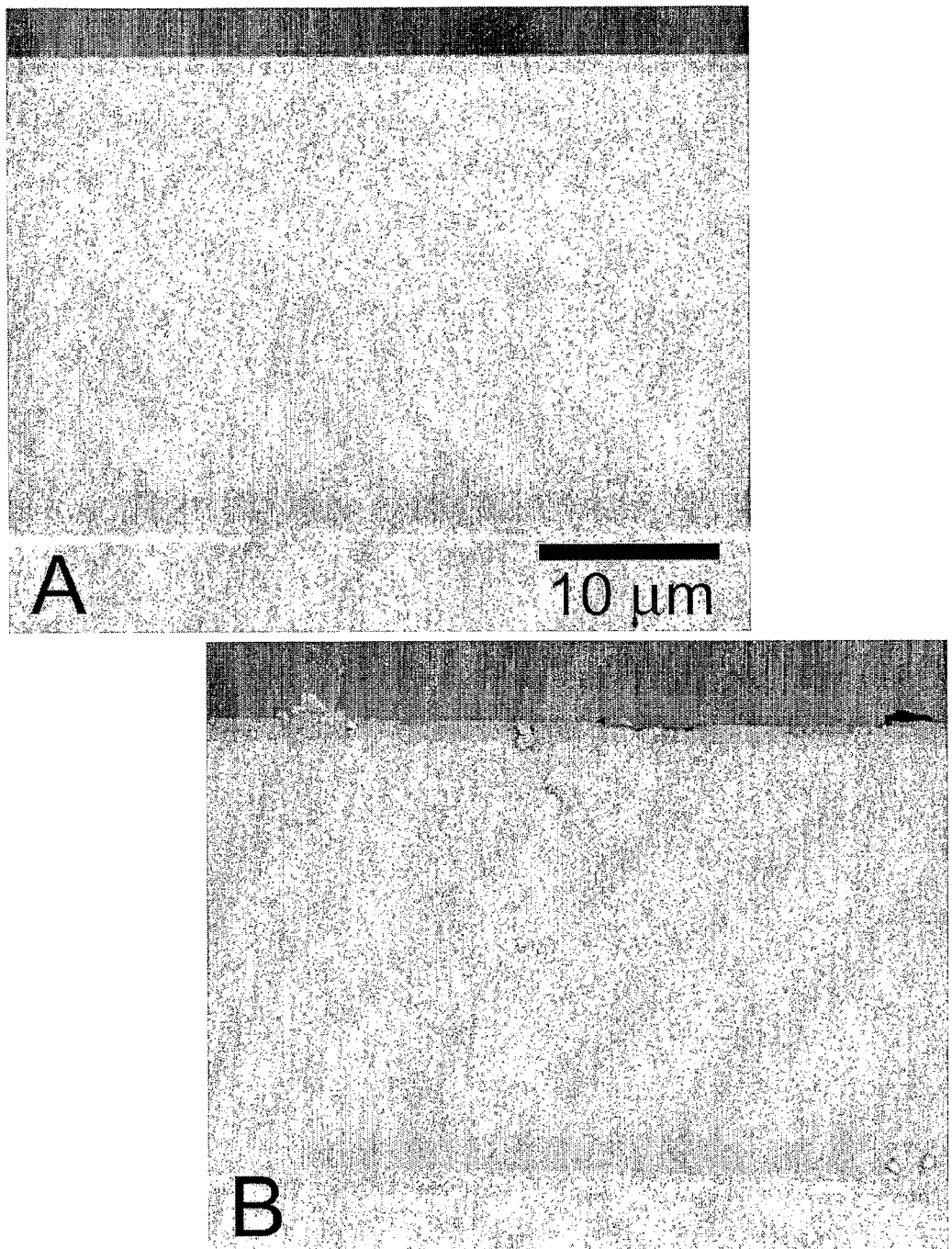
FIGS. 15a and 15b are cross-sectional scanning electron microscope (backscattered electron) images of porous Si photonic crystals, without (A) and with (B) caffeine microdomains.
Figure 16:
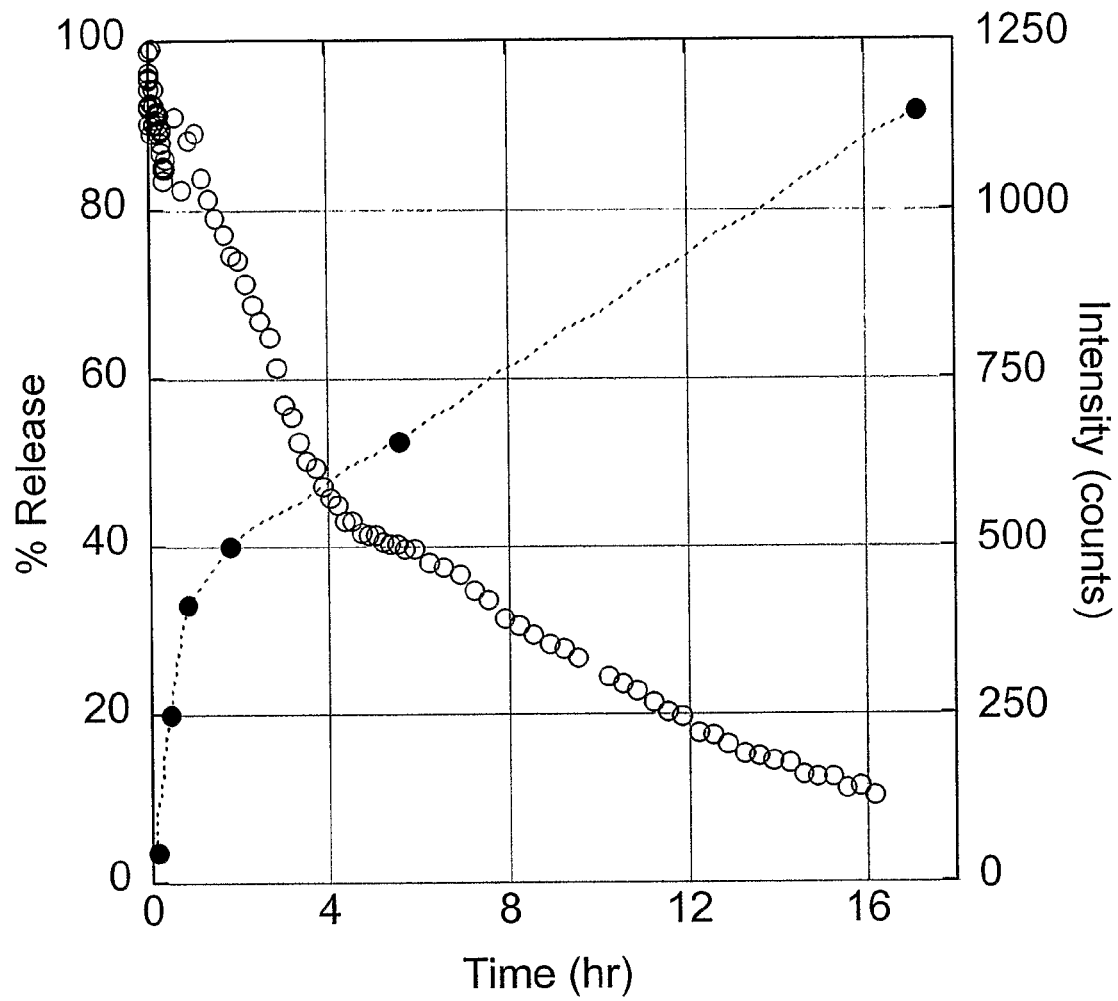
FIG. 16 is a graph illustrating intensity of the photonic peak scattered from a caffeine-impregnated porous Si photonic crystal sample (open circles) and percent of the loaded caffeine appearing in solution (solid circles) as a function of time in PBS solution.

Scanning electron microscopy (SEM) confirms the presence of sub micron-sized features in a porous Si photonic crystal that has been impregnated with caffeine (FIGS. 15a and 15b). Roughening of the surface of the film is also observed in some cases. When the sample is placed in an aqueous buffer solution, such as Dulbecco's phosphate buffered saline, pH 7.4, the intensity of the scattered photonic feature is observed to decrease over time, corresponding to leaching of the caffeine into solution (FIG. 16). After all the caffeine has been released, as determined by gravimetric and UV absorption measurements, the photonic feature from the porous Si host is still observable in the reflection spectrum taken along the specular reflection axis, although the intensity of the off-specular (scattered) feature is much weaker.

Figure 17:
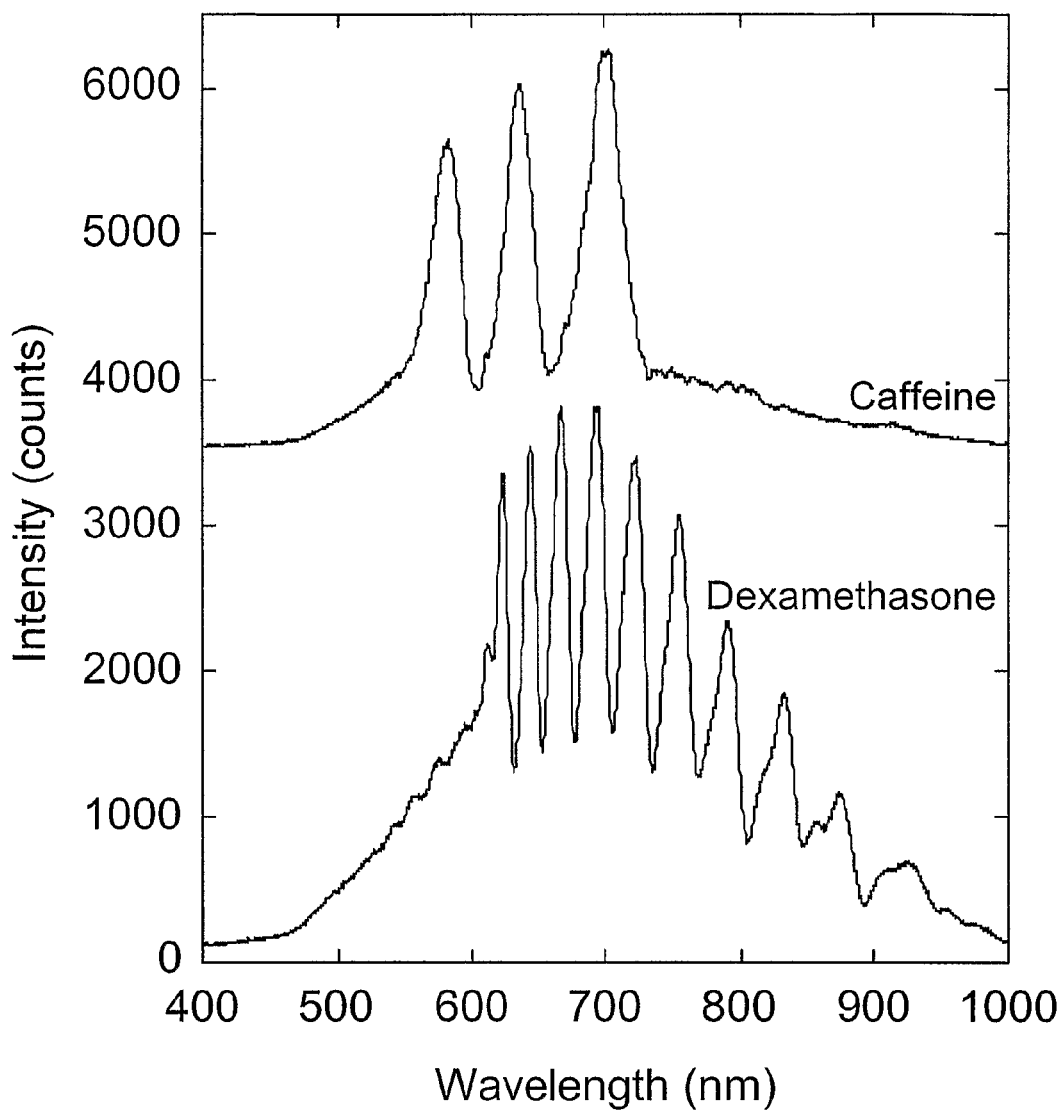
FIG. 17 is a graph illustrating scattered light spectra of drug-impregnated porous Si photonic crystals that have been prepared to display multiple diffraction peaks.

More elaborate spectral features can be incorporated into porous Si photonic crystals by applying a more complex current waveform to the Si sample during the etch. Such spectral "bar codes" allow ready identification of the sample, and can be used to monitor delivery of multiple drugs simultaneously if more than one porous Si host is used. FIG. 17 presents spectra of two porous Si samples prepared with different spectral barcodes, each infused with a different drug (dexamethasone and caffeine).

In summary, introduction of submicron-sized particles within the pores of a porous Si photonic crystal introduces scattering centers that distribute the resonance feature of the photonic crystal over a wide solid angle. If the scattering centers consist of microcrystallites of a drug, the scattering phenomenon can be used to monitor the rate of release of the drug from the porous matrix into a solution. The amount of drug released correlates to the intensity of the scattered photonic resonance in the visible spectrum. The ability to encode porous Si photonic crystals to allow simultaneous delivery and monitoring of multiple drugs is demonstrated.

Materials and Methods: Porous Si samples were prepared by anodic etch of degenerately B-doped p type, (100)-oriented Si with <1 mΩ·cm resistivity in a solution of 48% aqueous HF:ethanol (3:1 by volume). Encoded porous Si rugate structures were typically etched by applying a computer-generated current waveform.

Porous Si photonic crystals partially coated with polymer were prepared by spray-coating a solution of 16% polystyrene (av. M.W. 45,000) in toluene on the porous Si photonic crystal. The spray-coater consisted of a commercial artist's air brush and a filter membrane. The stream of fine droplets from the airbrush was impinged on a filter membrane containing sub-mm pores, and the sample was positioned behind this filter. This produced sub-mm domains of polymer on the porous Si substrate. The sample was then heated at 110° C. for 15 min.

Drugs were either cast or spin coated from methanol solutions into the porous Si photonic crystals. A typical caffeine-impregnated sample was prepared by depositing a preheated caffeine (99%) solution (0.03 M in methanol, 40° C.) onto the porous Si film for 15 sec and then spin-coating at 3000 rpm for 1 min. The above deposition process was repeated 6 times. The sample was then allowed to dry in air.

For the drug release experiments, the caffeine-impregnated porous Si sample was immersed in 25 ml of Dulbecco's phosphate buffered saline solution. Off-specular optical measurement was carried out by setting the spectrometer detector optics 5° away from the surface normal, while release of caffeine in the solution was monitored spectrometrically with a Hewlett-Packard 8452A diode array spectrometer.

Scanning electron microscope (SEM) images were obtained using an FEI Quanta 600 instrument operating at an accelerating voltage of 20 kV.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention. Exemplary claims are provided to illustrate preferred embodiments, and not to indicate the broadest scope of the invention.

What is claimed is:

1. A method of sensing the presence, quantity and morphology of a target analyte comprising:
    providing a porous substrate having a first optical signal;
    filling the pores of the porous substrate with polystyrene;
    exposing the porous substrate to an environment suspected of containing the target analyte;
    monitoring changes in the first optical signal over time;
    monitoring an intensity of the optical signal to determine morphology of the analyte.

2. The method of claim 1 further comprising providing one of a porous Si substrate, porous alumina substrate, porous Ge substrate, porous GaAs substrate, porous SiO$_2$ substrate and a porous polymer substrate.

3. The method of claim 1 further comprising exposing the porous substrate to a target analyte from the group consisting of chemicals, cells, viruses, toxins, macromolecules, proteins, polymers, biomolecules and biopolymers.

4. The method of claim 1 further comprising chemically functionalizing a surface of the porous substrate to target a specific analyte.

5. The method of claim 4 further comprising hydrosilylating the surface of the porous substrate.

6. The method of claim 4 further comprising chemically functionalizing the surface with one of the group consisting of proteins, carbohydrates, antibodies, and cells.

7. The method of claim 1 further comprising monitoring a spectral distribution of the optical signal to determine whether the analyte or a product of the analyte has entered the pores of the porous substrate.

8. The method of claim 1 further comprising monitoring the first optical signal by one of a white light source and a CCD spectrometer, a white light source and a digital imaging system, an LED and a photocell, a laser and a photocell, visual inspection, and visual inspection with a microscope.

9. A cell-based biological and chemical sensor for detecting the presence, quantity, status and morphology of a cell and products of the cell comprising:
    a porous substrate having a pore size, porosity gradient and a chemically functionalized surface to specifically target a cell type, wherein the porous substrate produces a first optical signal prior to exposure to the cell type, and further comprising polymer impregnated in the pores of the porous substrate; and
    a signal detector.

10. The sensor of claim 9 further comprising a porous substrate composed of a material selected from the group consisting of porous Si, porous GaAs, porous SiO$_2$, and porous polymer.

11. The sensor of claim 9 wherein said chemically functionalized surface is hydrosilylated to be capped with a hydrocarbon chain and a carboxylic acid terminal group.

12. The sensor of claim 9 wherein said polymer comprises polystyrene.

13. The sensor of claim 9 wherein said signal detector comprises one of the combinations selected from the group consisting of a white light source and a CCD spectrometer, a white light source and a digital imaging system, an LED and a photocell, visual inspection, and visual inspection with a microscope.

14. A method of real-time sensing and monitoring cellular activity comprising:
    providing photonic crystals having a first optical signal;
    chemically functionalizing surfaces of the photonic crystals to target specific cells or biomolecules;
    measuring the first optical signal of the photonic crystals;
    exposing the photonic crystals to an environment suspected of containing the target cells or biomolecules;
    measuring a second optical signal of the photonic crystals after exposure to the environment suspected of containing target cells or biomolecules; and
    observing changes in the first and second optical signals to determine the presence, morphology and health of the target cells or biomolecules.

15. The method of claim 14 wherein the target cells or biomolecules include one or more of the group consisting of mammalian cells, bacterial cells, proteins, toxins and viruses.

16. The method of claim 14 wherein measurement of the first and second optical signals comprises impinging a light source on a surface of the photonic crystal and measuring scattering efficiency and specular distribution.

17. A method of monitoring controlled drug release over time comprising:
- providing a porous film having a first optical signal;
- measuring the first optical signal of the porous film;
- impregnating the porous film with a predetermined drug or drug combination;
- measuring a second optical signal of the photonic crystals after said impregnating; and
- observing changes in the first and second optical signals to determine an amount of release of the predetermined drug or drug combination.

18. The method of claim 17 wherein the porous film comprises one of a porous Si film, porous $SiO_2$ film, and a porous polymer film.

19. A method of sensing the presence, quantity and morphology of a target analyte comprising:
- providing a porous substrate having a characteristic optical signal measured;
- exposing the porous substrate to an environment suspected of containing the target analyte;
- illuminating a surface of the porous substrate to stimulate reflections from the porous substrate;
- measuring scattered light at an off-specular measurement axis to ascertain the presence or absence and morphology of the target analyte.

20. The method of claim 19, comprising repeating said measuring to ascertain changes in the presence or absence an morphology of the target analyte.

21. The method of claim 19, wherein said further comprising determining intensity of one or more peaks in an off-specular axis reflection spectra and conducting spectral analysis.

* * * * *

UNITED STATES PATENT AND TRADEMARK OFFICE
CERTIFICATE OF CORRECTION

PATENT NO. : 7,903,239 B2  Page 1 of 1
APPLICATION NO. : 11/665613
DATED : March 8, 2011
INVENTOR(S) : Sailor et al.

It is certified that error appears in the above-identified patent and that said Letters Patent is hereby corrected as shown below:

On the Title Page:

In the Second Column          On page 2, delete the 23rd item in the first column:
(56) References Cited            "2006/0105043 A1 5/2006 Sailor" and replace it with
U.S. PATENT DOCUMENTS         --2006/0105043 A1 5/2006 Sailor et al.--
(*Continued on Page 2*)

| | | |
|---|---|---|
| Col. 2 | Line 13 | Delete "(e)" and insert --(c)-- therefor. |
| Col. 2 | Line 20 | Delete "peaks" and insert --peak-- therefor. |
| Col. 4 | Line 26 | Insert a --.-- after "physiology". |
| Col. 10 | Line 67 | After "images" delete "of". |

Signed and Sealed this
Sixteenth Day of August, 2011

David J. Kappos
*Director of the United States Patent and Trademark Office*